US006875423B1

(12) United States Patent
Intaglietta et al.

(10) Patent No.: US 6,875,423 B1
(45) Date of Patent: Apr. 5, 2005

(54) METHODS FOR INCREASING PERIPHERAL BLOOD CIRCULATION

(76) Inventors: Marcos Intaglietta, 5888 Ravenswood Rd., La Jolla, CA (US) 92037-7419; Vladimir P. Torchilin, 12 Shipway Pl., Charlestown, MA (US) 02129; Vladimir S. Trubetskoy, 7435 Hunters Ct., Middleton, WI (US) 53562; Amy G. Tsai, 5582-2 Renaissance Ave., San Diego, CA (US) 92122

(*) Notice: Subject to any disclaimer, the term of this patent is extended or adjusted under 35 U.S.C. 154(b) by 195 days.

(21) Appl. No.: 09/667,335

(22) Filed: Sep. 21, 2000

Related U.S. Application Data

(60) Provisional application No. 60/154,996, filed on Sep. 21, 1999.

(51) Int. Cl.[7] ............................................. A61K 31/721
(52) U.S. Cl. ........................................................ 424/59
(58) Field of Search .......................................... 514/59

(56) References Cited

U.S. PATENT DOCUMENTS

| 5,057,313 A | 10/1991 | Shih et al. |
| 5,814,601 A | 9/1998 | Winslow et al. |
| 5,985,825 A | 11/1999 | Winslow et al. |
| 6,054,427 A | 4/2000 | Winslow |

OTHER PUBLICATIONS

Krieter et al., Acta Anaesthesiologica Scandinavica 39(2):236–244 (1995). Abstract.*
Ehrly et al., Bibliotheca Anatomica 13:122–126 (1975). Abstract.*
Frangos et al. (1985) Flow Effects on Prostacyclin Production by Cultured Human Endothelial Cells, Science 227:1477–1479.
de Wit et al. (1997) "Elevation of plasma viscosity induces sustained NO–mediated dilation in the hamster cremaster microcirculation in vivo," Phyugers Arch. 434–354–361.
Malek (1999) "Induction of Nitric Oxide Synthase mRNA by Shear Stress Requires Intracellular Calcium and G–protein Signals and Is Modulated by PI 3 Kinase," Biochem. Biophys. Res. Comm. 254:231–242.
Dimmeler (1998) "Fluid Shear Stress Stimulates Phosphorylation of Akt in Human Endothelial Cells," Circ. Res. 83:334–341.
Deb et al. (1999) "Resuscitation with Lactated Ringer's Solution in Rats with Hemorrhagic Shock Induces Inmediate Apoptosis," J. Trauma 46:582–589.
Richardson and Guyton (1959) "Effects of polycythemia and anemia on cardiac output and other circulatory factors," Am. J. Physiol. 197:1167–1170.
Messmer (1975) "Hemodilution" Surg. Clins N. Am. 55:659–78.

Mirhashemi et al. (1987) "Microcirculatory effects of normovolemic hemodilution in skeletal muscle," Int. J. Microcirc.: Clin.Exp. 6:359–369.
Johnson (1986) "Autoregulation of Blood Flow," Circ. Res. 59:483–495.
Lindbom and Arfors (1980) "Influence of Oxygen on Perfused Capillary Density and Capillary Red Cell Velocity in Rabbit Skeletal Muscle," Microvasc. Res. 19:197–208.
Tsai et al. (1998) "Plasma viscosity regulates capillary perfusion during extreme hemodilution in hamster skinfold model," Am. J. Physiol. 275:H2170–H2180.
Kerger et al. (1996) "Systemic and subcutaneous microvascular $PO_2$ dissociation during 4–h hemorrhagic shock in conscious hamsters," Am. J. Physiol. 279:H827–H836.
Schmid Schönbein & Sweifach (1975) "RBC Velocity Profiles in Arterioles and Venules of the Rabbit Omentum," Microvasc Res. 10:153–164.
Fung et al. (1970) "Elastic Environment of the Capillary Bed," Circ. Res. 19:441–461.
Intaglietta & dePlomb (1973) "Fluid Exchange in Tunnel and Tube Capillaries," Microvasc. Res. 6:153–168.
Secomb et al. (1987) "Effects of Reduced Perfusion and Hematocrit on Flow Distribution in Capillary Networks," Prog. Appl. Microcirc. 12:205–211.
Mazzoni et al. (1990) "The Efficacy of Iso– and Hyperosmotic Fluids as Volume Expanders in Fixed–Volume and Uncontrolled Hemorrhage," Ann. Emerg. Med. 19:350–358.
Tsai et al. (1991) "Spatial distribution of red blood cells in individual skeletal muscle capillaries during extreme hemodilution," Int. J. Microcirc.: Clin. Exp. 10:317–334.
Waschke et al. (1994) "Lack of Dependence of Cerebral Blood Flow on Blood Viscosity After Blood Exchange with a Newtonian $O_2$ Carrier," J. Cerebral Blood Flow and Metab. 14:871–876.
Krieter et al. (1995) "Does colloid–induced plasma hyperviscosity in haemodilution jeopardize perfusion and oxygenation of vital organs?" Acta Anaest. Scand. 39:236–244.
Herrmann et al. (1997) "Shear Stress Inhibits $H_2O_2$–Induced Apoptosis of Human Endothelial Cells by Modulation of the Glutathione Redox Cycle and Nitric Oxide Synthase," Arterioscler. Thromb. Vasc. Biol. 17:3588–3592.
Dimmeler et al. (1999) "Upregulation of Superoxide Dismutase and Nitric Oxide Synthase Mediates the Apoptosis–Suppressive Effects of Shear Stress on Endothelial Cells," Arterioscler. Thromb. Vasc. Biol. 19:656–664.

(Continued)

Primary Examiner—Jean C. Witz
(74) Attorney, Agent, or Firm—Medlen & Carroll, LLP

(57) ABSTRACT

Methods and compositions are described which are useful for increasing the peripheral blood flow in mammals during conditions of hemodilution. The methods and compositions involve the use of materials to increase the blood viscosity in the system of microscopic blood vessels.

41 Claims, 6 Drawing Sheets

OTHER PUBLICATIONS

Xie et al. (1996) "Role of Endothelium–Derived Nitric Oxide in the Modulation of Canine Myocardial Mitochondrial Respiration In Vitro," Circ. Res. 79:381–387.

Intaglietta and Zweifach (1973) "Microcirculatory Basis of Fluid Exchange," Advances in Biol. and Med. Phys. 15:111–159.

Kanzow et al. (1982) "Analysis of the hematocrit distribution in the mesenteric microcirculation," Intl. J. Microcirc. Clin. Exp. 1:67–79.

Klitzman and Johnson (1982) "Capillary network geometry and red cell distribution in hamster cremaster muscle," Am. J. Physiol. 242:H211–H219.

Lipowsky et al. (1980) "In vivo measurements of hematocrit and apparent viscosity in the microvasculature of cat mesentery," Microvasc. Res. 29:297–319.

Lipowsky, "Mechanics of Blood Flow in the Microcirculation," Chapter18, in *Handbook of Bioengineering,* Skalak and Chien, eds., McGraw–Hill Book Co., NY, 1987.

Sarelius and Duling (1982) "Direct measurement of microvessel hematocrit, red cell flux, velocity and transit time," Am. J. Physiol. 243:H1018–H1026.

Intaglietta et al. (1975) "Capillary Flow Velocity Measurements In Vivo and In Situ by Television Methods," Microvasc. Res. 10:165–179.

Messmer et al. (1972) "Circulatory Significance of Hemodilution: Rheological Changes and Limitations," Adv. Microcirc. 4:1–77.

Lipowsky and Firrell (1986) "Microvascular hemodynamics during systemic hemodilution and hemoconcentration," Am. J. Physiol. 250:H908–H922.

Mirhashemi et al. (1988) "Effects of hemodilution on skin microcirculation," Am. J. Physiol. 254:H411–H416.

Tigno and Henrich (1986) "Flow Characteristics of the Microcirculation Following Intentional Hemodilution," Acta. Med. Phil. 22:5–12.

Tigno and Henrich (1986) "Flow Characteristics of the Microcirculation Following Intentional Hemodilution, Part II. Hemodynamic response of the pre–capillary arterioles," Acta. Med. Phil. 22:53–58.

Gustafsson et al. (1981) "Effects of increased plasma viscosity and red blood cell aggregation on blood viscosity in vivo," Am. J. Physiol. 241:H513–H518.

Barbee and Cokelet (1971) "The Fahraeus Effect," Microvasc. Res. 3:6–16.

Buga et al. (1991) "Shear Stress–Induced Release of Nitric Oxide From Endothelial Cells Grown on Beads," Hypertension 17:187–193.

Colantuoni et al. (1984) "Quantitation of rhythmic diameter changes in arterial microcirculation," Am. J. Physiol. 246:H508–H517.

Neumann et al. (1980) "A New Highly Potent and Short–acting Analgesic, Carfentanyl (R33799), in Combination with the Hypnotic Agent, Etornidat (R26490), as a Method of Anaesthesia in Guinea Pigs," Res. Exp. Med. (Berl) 177:135–143.

Lipowsky and Zweifach (1978) "Application of the "Two–Slit" Photometric Technique to the Measurement of Microvascular Volumetric Flow Rates," Microvasc. Res. 15:93–101.

Filho et al. (1993) "Microvessel $PO_2$ measurements by phosphorescence decay method," Am. J. Physiol. 34:H1434–H1438.

Wilson (1993) "Measuring Oxygen Using Oxygen Dependent Quenching of Phosphorescence: A Status Report," Adv. Med. Biol. 333:225–232.

Vanderkooi et al. (1987) "An Optical Method for Measurement of Dioxygen Concentration Based upon Quenching of Phosphorescense," J. Biol. Chem. 252:5476–5482.

Chien and Jan (1973) "Red Cell Aggregation by Macromolecules: Roles of Surface Adsorption and Electrostatic Repulsion," J. Supramol. Struct. 12:385–409.

Gelin (1956) "Studies in Anemia of Injury," Acta Chir. Scand. Suppl. 210:1–130.

Kroemer et al. (1987) "Haemodilution Therapy in Ischaemic Stroke: Plasma Concentrations and Plasma Viscosity During Long–Term Infusion of Dextran 40 or Hydroxyethyl Starch 200/0.5," Euro J. Clin. Pharm. 31:705–710.

Bruckner et al. (1993) "Organ Blood Supply and Tissue Oxygenation after Limited Normovolemic Hemodilution with 3% versus 6% Dextran–60," Infusionstherapie und Transfusionmedizin 20:130–139.

Schmidt et al. (1993) "Hyperoncotic Ultrahigh Molecular Weight Dextran Solutions Reduce Trypsinogen Activation, Prevent Acinar Necrosis, and Lower Mortality in Rodent Pancreatitis," Am. J. Surg. 165:40–45.

Chen et al. (1989) "Effects of dextran–induced hyperviscosity on regional blood flow and hemodynamics in dogs," Am. J. Physiol. 256:H898–H905.

Doss et al. (1995) "Mechanism of Systemic Vasodilation During Normovolemic Hemodilution," Anesthesia and Analgesia 81:30–34.

Intaglietta (1997) "Whitaker Lecture 1996: Microcirculation, Biomedical Engineering, and Artificial Blood," Ann. Biomed. Eng. 25:593–603.

Smieško and Johnson (1993) "The Arterial Lumen Is Controlled by Flow–Related Shear Stress," NIPS 8:34–38.

Kuo and Pittman (1988) "Effect of hemodilution on oxygen transport in arteriolar networks of hamster striated muscle," Am. J. Physiol. 254:H331–H339.

Hudak et al. (1989) "Hemodilution cases size–dependent constriction of pial arterioles in the cat," Am. J. Physiol. 257:H912–H917.

Colantuoni et al. (1984) "Effects of anaethesia on the spontaneous activity of the microvasculature," Int. J. Microcirc. Clin. Exp. 3:13–28.

Funk and Baldinger (1995) "Microcirculatory Perfusion during Volume Therapy," Anethesiology 82:975–982.

Nolte et al. (1997) "Effects of diaspirin–cross–linked hemoglobin (DCLHb™) on local tissue oxygen tension in striated skin muscle: An efficacy study in the hamster," J. Lab. Clin. Med. 130:328–338.

Hint (1968) "The pharmacology of dextran and the physiological background for the clinical use of Rheomacrodex and Macrodex," Acta Anaes. Begl. 19:119–138.

Mirhashemi et al. (1987) "Tissue perfusion during normovolemic hemodilution investigated by a hydraulic model of the cardiovascular system," Int. J. Microcirc. Clin. Exp. 6:123–136.

Jackson and Duling (1983) "The Oxygen Sensitivity of Hamster Cheek Pouch Arterioles," Circ. Res. 53:515–525.

\* cited by examiner

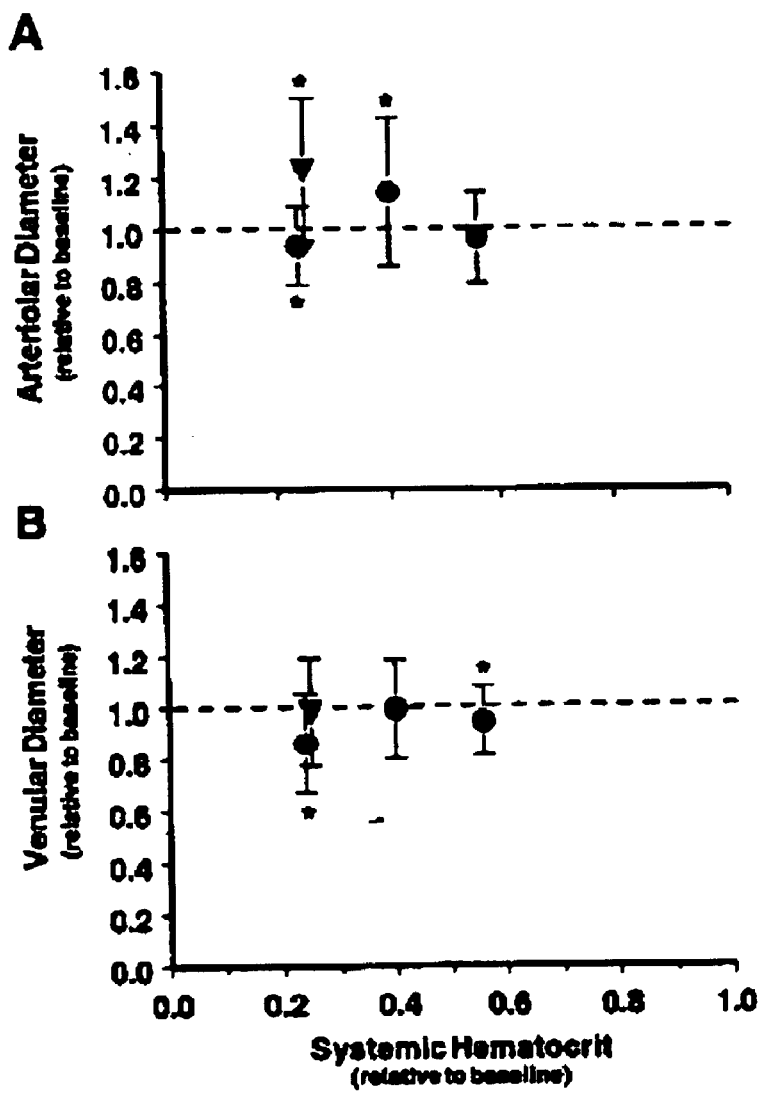
Fig. 2. Vascular tone vs. systemic hematocrit. Data are presented as means ± SD. ●, Dextran 70 exchange; ▼, Dextran 500 exchange. Broken line represents baseline level. *$P < 0.05$. Baseline diameters (μm) in each animal group were as follows: level 1 [arterioles (A): 62.4 ± 18.2, n = 44, venules (V): 68.8 ± 37.5, n = 42]; level 2 (A: 57.9 ± 17.8, n = 46, V: 70.9 ± 39.2, n = 38); level 3 LV (A: 58.6 ± 12.3, n = 49, V: 78.5 ± 23.9, n = 37); level 3 HV (A: 57.4 ± 15.3, n = 47, V: 68.9 ± 32.7 n = 38). n, No. of vessels studied.

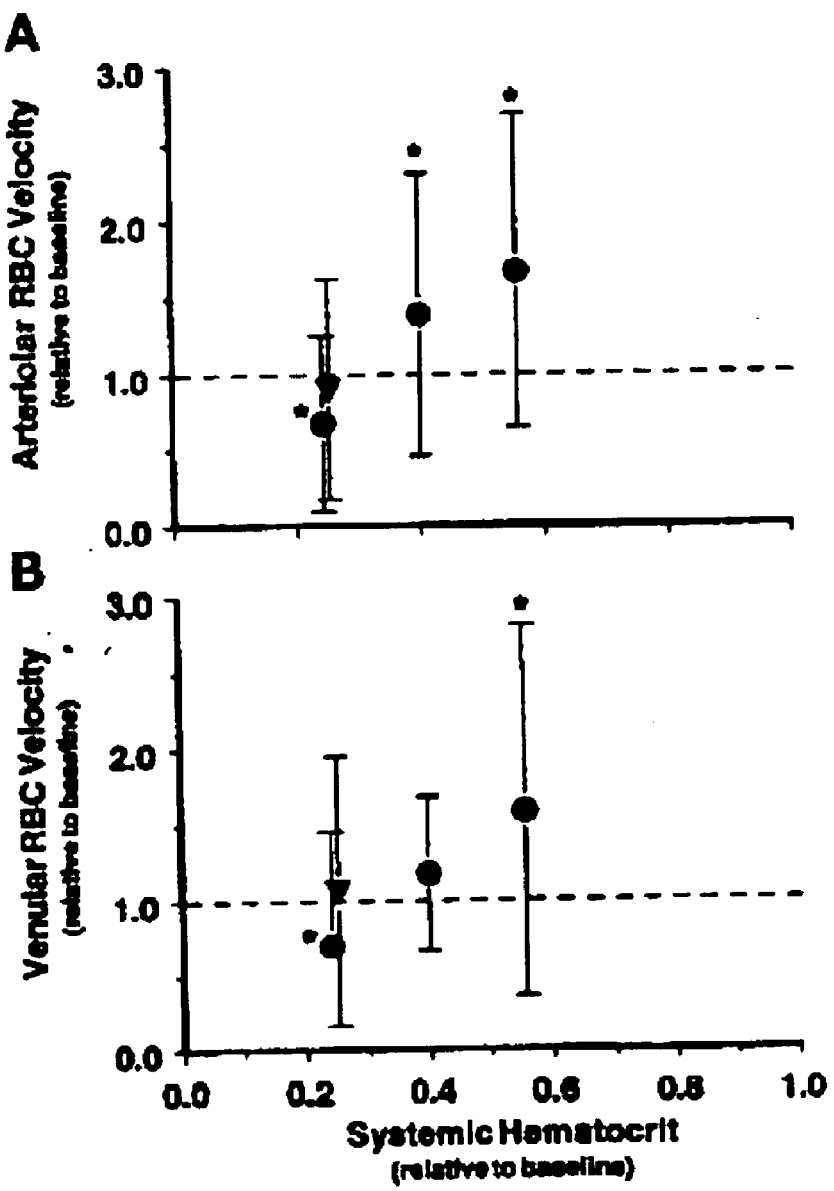

Fig. 3. Arteriolar and venular red blood cell (RBC) velocity vs. systemic hematocrit. Initial increase in arteriolar RBC velocity was followed by a return to baseline with HV protocol, whereas LV protocol led to a reduced RBC velocity. Similar pattern was observed in venular RBC velocity except the return to baseline levels was earlier, occurring after the second exchange. Data are presented as means ± SD. ●, Dextran 70 exchange; ▼, Dextran 500 exchange. Broken line represents baseline level. *$P < 0.05$. Baseline RBC velocities (mm/s) in each animal group were as follows: control (A: 4.9 ± 3.8, V: 1.0 ± 0.7); level 1 (A: 4.3 ± 2.4, V: 1.2 ± 0.8); level 2 (A: 4.5 ± 2.5, V: 1.2 ± 1.4); level 3 LV (A: 4.0 ± 2.3, V: 1.0 ± 0.8); level 3 HV (A: 4.1 ± 2.7, V: 1.1 ± 0.9).

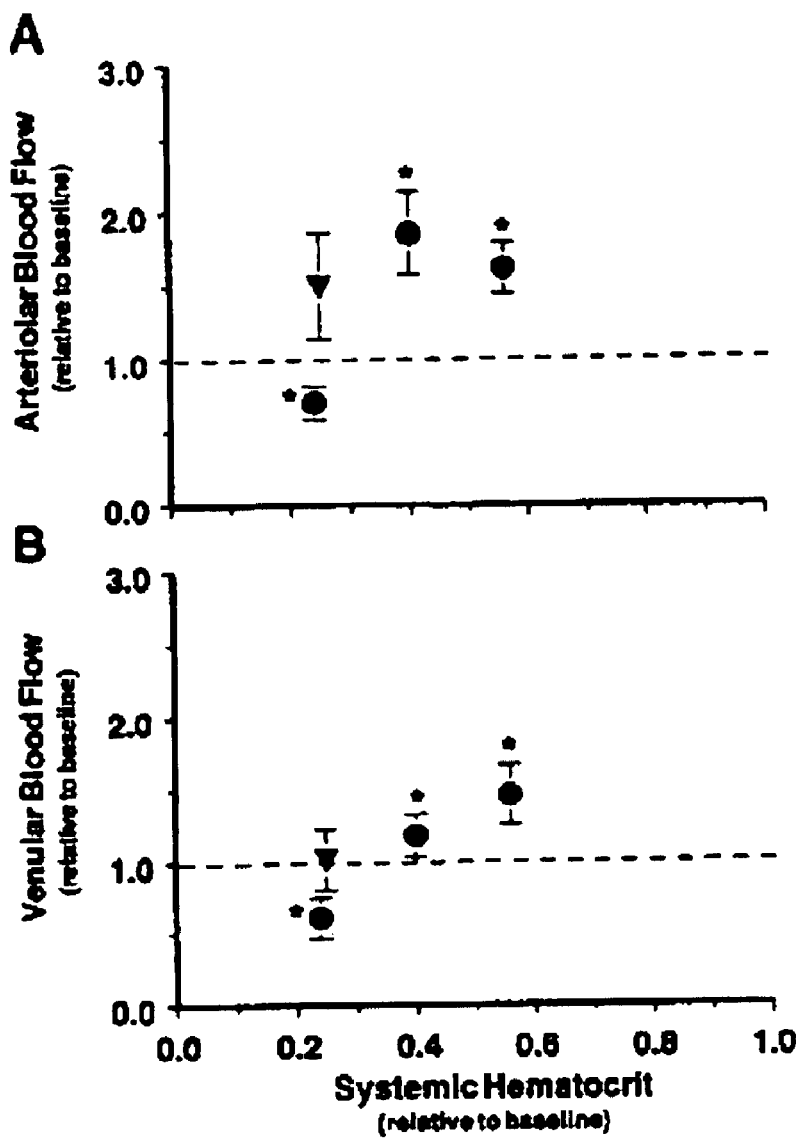

Fig. 4. Arteriolar and venular blood flow vs. systemic hematocrit. Hemodilution led to initial increases in blood flow in both vessel types. At the *level 3* exchange, HV protocol was able to maintain blood flow at baseline levels, whereas LV protocol resulted in reduction. Data are presented as means ± SE relative to baseline levels. ●, Dextran 70 exchange; ▼, Dextran 500 exchange. Broken line represents baseline level. *$P < 0.05$.

Figure 5

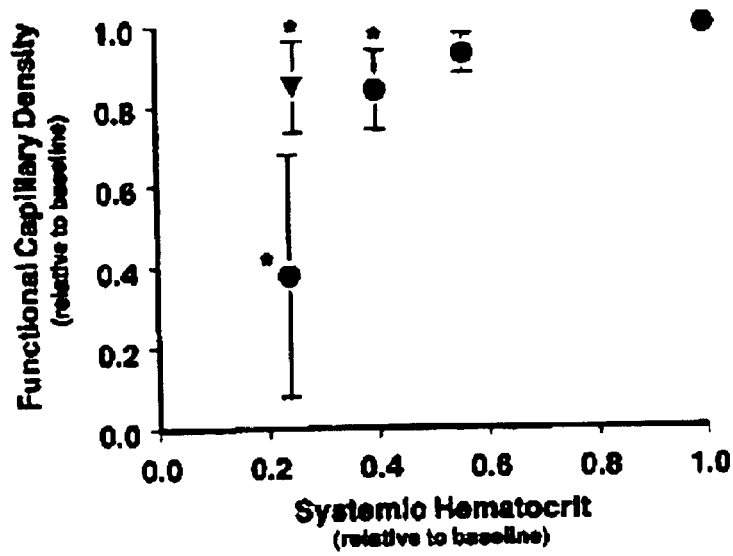

Fig. 5. Effect of hemodilution on capillary perfusion. Functional capillary density (FCD) was unchanged after *level 1* exchange. Drop in FCD was greater after *level 3* LV than *level 3* HV exchange. Data points are means ± SD relative to baseline. ●, Dextran 70 exchange; ▼, Dextran 500 exchange. *$P < 0.05$. Baseline FCD ($cm^{-1}$) in each experimental group was as follows: *level 1* (105.8 ± 22.1); *level 2* (121.2 ± 20.9); *level 3* LV (109.2 ± 22.2); *level 3* HV (107.6 ± 22.3).

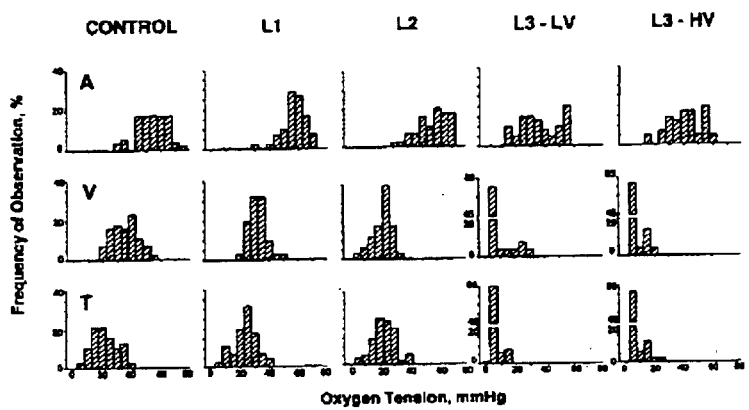

Fig. 6. Distribution of microvascular $PO_2$ vs. hemodilution level. A, arterioles; V, venules; T, tissue. Shift in arteriolar $PO_2$ to the right and venular $PO_2$ shift to the left after level 1 and 2 exchange maintained tissue oxygenation at baseline levels. Level 3, extreme hemodilution, resulted in significant reduction across all categories. Both level 3 LV and level 3 HV caused a significant reduction in $PO_2$ in all categories. $PO_2$ measurements could only be made in vessels that had blood flow; thus the histograms for level 3 LV do not include data from 2 animals that did not have blood flow in the tissue under study. Control group vessel diameters (means ± SD, μm) were A: $57.0 \pm 18.5$ ($n = 58$), V: $69.9 \pm 35.3$ ($n = 56$), and RBC velocities (mm/s) were A: $4.9 \pm 3.8$ ($n = 58$), V: $1.0 \pm 0.7$ ($n = 56$). n, No. of vessels studied.

METHODS FOR INCREASING PERIPHERAL BLOOD CIRCULATION

RELATED APPLICATION

This application claims the benefit of Intaglietta et al., U.S. Provisional Application No. 60/154,996, filed Sep. 21, 1999, entitled METHODS FOR INCREASING PERIPHERAL BLOOD CIRCULATION, which is hereby incorporated by reference in its entirety, including drawings.

BACKGROUND OF THE INVENTION

This invention relates to the field of medical treatment involving blood transfusions and the use of blood expanders or substitutes. The description provided herein is provided solely to assist the understanding of the reader. None of the information provided or references cited is admitted to be prior art to the present invention.

A variety of blood substitutes or plasma expanders have been described. Commonly blood substitutes are perfluorocarbon-based emulsions, liposome-encapsulated hemoglobin, or modified hemoglobin.

Also described is a blood substitute which specifically includes both oxygen-carrying and non-oxygen-carrying plasma expanders (Winslow & Intaglietta, U.S. Pat. No. 5,814,601). Typically the oxygen-carrying component is a modified hemoglobin and the non-oxygen-carrying component is a starch.

SUMMARY OF THE INVENTION

The present invention concerns materials and methods which are particularly useful for maintaining or increasing the peripheral blood flow in a mammal, thereby providing effective perfusion of tissues. By maintaining proper perfusion, cellular and tissue integrity is also maintained, even in the presence of high degrees of hemodilution, e.g., hematocrit reduced by up to 50%, 60%, 70%, 75%, or even 80% from normal. Effective perfusion maintains the removal of cellular waste products, thereby avoiding apoptotic or necrotic cell destruction due to build-up of such waste products. It was discovered that current artificial blood products and blood expanders do not effectively maintain peripheral blood flow, as they typically have too low a viscosity. Therefore, administration of solution of a biocompatible material which allows the viscosity of the blood to be maintained above the level at which arteriolar vasoconstriction and capillary narrowing or occlusion occurs provides substantial patient benefit. Generally, for humans such vasoconstriction will occur at approximately 2 centipoise (cp), so the administered solution contains sufficient viscosity increasing agent to maintain blood viscosity above that level. In general, the solutions of the present invention do not contain a separate oxygen carrying component, and preferably the viscosity-increasing agent is not also an oxygencarrying material, where the term "oxygen carrying" is used in the sense commonly applied in the field of artificial blood products.

Thus, in a first aspect, the invention provides a method for increasing plasma viscosity in a mammal by administering a pharmaceutically acceptable viscosity-increasing agent in an amount sufficient to increase plasma viscosity by at least 0.5 centipose (cp), preferably at least 1.0 cp, more preferably at least 1.5 cp, still more preferably at least 2.0 cp or at least 2.5 cp. Preferably the viscosity-increasing agent is administered in a solution of sufficient viscosity such that on dilution into the blood of the mammal the resulting blood viscosity is maintained above 2 cp, and preferably above 3 cp, or more preferably in the range of 3–5 cp, most preferably 3.5–4.5 cp.

In preferred embodiments, the administered solution has a viscosity of 3–30 cp or 5–25 cp, preferably 7–20 cp, more preferably 10–17 cp, and most preferably 12–15 cp. However, in particular applications, other starting viscosities may be beneficial, e.g., other viscosities as specified herein for the solutions of viscosity-increasing agents. Usually, the viscosity-increasing agent will be administered intravenously.

In preferred embodiments, the mammal is a large mammal, such as a sheep, swine, bovine, horse, chimpanzee, monkey, ape, or human. In other embodiments, the mammal is a dog or cat.

In preferred embodiments, the hematocrit of the mammal is decreased at least 40% or 50% prior to or following administration of the viscosity-increasing agent, as compared to normal for that mammalian species or for that individual. The decrease may, for example, be due to hemodilution from use of plasma expanders or to pathologic loss of red blood cells. In other embodiments, the decrease in hematocrit is at least 60%, 70%, 75%, or 80%.

In preferred embodiments, the administration of the viscosity-increasing agent delays or eliminates the need for a blood transfusion.

The term "plasma viscosity" refers to the viscosity of cell-free plasma of a mammal.

In the context of this invention, the term "viscosity increasing agent" refers to a compound or mixture of compounds which increases the viscosity of plasma when combined with that plasma and which is biocompatible in the form administered. Unless specifically indicated to the contrary, a "viscosity increasing agent" is not also an oxygen-carrying agent.

By "biocompatible" is meant that the agent, in the form and concentration used, is not toxic to cells and does not result in other biological damage to the organism which would preclude use of the material by a prudent medical practitioner. Highly preferably, the viscosity increasing agent does not include any oxygen-carrying component. As pointed out above, it is highly preferred that the compositions of this invention do not include an oxygen-carrying agent or component.

In the form to be administered to a patient, the viscosity-increasing agent (and a solution containing the agent) is highly preferably "sterile." This means that the material is free from viable organisms or cells at a confidence level acceptable for approval of the material for use in the relevant mammal, e.g., for use in humans. Preferably, for human use, the material is approved by the Food and Drug Administration and/or the European or Japanese regulatory authority having oversight of such products.

The viscosity-increasing agent is distinct from agents previously used for applications such as contrast enhancement agents, solubilizing agents, drugs, and the like. For example, contrast enhancement agents are generally used in solution volumes of about 25 ml or less, while solutions containing the present viscosity-increasing agents are generally used in solution volumes of 100 ml or greater, more often 200, 300, 400, or 500 ml, e.g., such an amount will be administered to an individual in a single treatment administration. The solution provides a distinct increase in peripheral blood viscosity in the quantities utilized rather than merely a small incidental increase.

Typically, the viscosity-increasing agent will be a high molecular weight compound or mixture of high molecular weight compounds. The term "high molecular weight" refers to molecular weights in excess of 5,000 daltons, preferably in excess of 10,000 daltons, still more preferably in excess of 30,000, 50,000, 70,000, or 100,000 daltons, and most preferably in excess of 150,000, 200,000, 300,000, 400,000, 500,000 daltons or even more than 500,000 daltons. Typically, the solutions to be used will have a viscosity of 3 to 30 cp, preferably 5 to 25 or 8 to 25 cp, more preferably 10 to 20 cp and most preferably 12 to 20 cp. In other embodiments, the solution has a viscosity of 8 to 15 cp or 10 to 18 cp, or 17 to 22 cp.

The term "amount" in connection with administration of a viscosity-increasing agent includes the absolute quantity of the agent and, if the agent is in a solution or suspension, also includes the concentration of the agent and/or volume of the solution containing the agent. The concentration of a solution or suspension is significant as the solution will dilute into the blood of the mammal and the final concentration or viscosity of the plasma is relevant.

The terms "injection", "intravenous", "intraarterial" and similar terms indicating administration of a solution of the invention include administration using syringes, pumps, gravity feed, and other methods of administering liquids as recognized by those skilled in the art. Specifically, the term "injection" includes other delivery modes and is not limited to syringe injection unless specifically stated.

In connection with the viscosity-increasing agents, solutions, and compositions of this invention, the term "administering" refers to placing the material within the circulatory system of an animal, directly or indirectly. In most cases the administration will be directly, e.g., by pumping or gravity flow of a solution directly into the circulatory system of the animal. However, the administration may also be indirect, such as where the solution is added to blood or other solution externally to the body of an animal and the combination is directed into the circulatory system of the animal.

In reference to a blood transfusion, the term "delay" refers to a decrease or lowering in the hematocrit level at which transfusion is medically necessary. Generally such as shift will also result in a temporal delay in the need for transfusion. In many cases, the shift will have the result that no transfusion will be needed, as the tissue perfusion is sufficiently maintained using the present solutions, though transfusion would have been needed if the viscosity-increasing agent had not been administered.

As used herein, the term "hematocrit" refers to the concentration of red blood cells in the blood of an animal, and provides a measure of the normal hemoglobin available for oxygen transport. The hematocrit can be determined by routine methods.

In another aspect, the invention provides a method for maintaining or increasing capillary blood flow in a mammal by increasing plasma viscosity by administering to the mammal a pharmaceutically acceptable viscosity-increasing agent in an amount sufficient to increase plasma viscosity by at least 0.5 cp, 1.0 cp, 1.5 cp, 2.0 cp, or 2.5 cp. Preferably, the capillary blood flow is maintained or increased by maintaining or increasing the functional capillary density (FCD).

The term "functional capillary density" or "FCD" refers to the number of capillaries per unit volume of tissue through which there is transit (flow) of red blood cells and/or plasma. FCD can be determined in various ways, including as described herein. In some cases it is useful to determine the relative change in FCD.

As above, the mammal is preferably a large mammal such as a swine, sheep, bovine, horse, chimpanzee, ape, or human, or is a dog, cat, or monkey. Preferably the mammal is a human.

Preferably the increase in plasma viscosity results in an increase in peripheral blood flow of at least 25%, more preferably at least 30%, 40%, 50%, 75%, 100% or even more. In other embodiments, the peripheral blood flow is maintained at a level at least 30% of normal, or at least 40%, 50%, 60%, 70%, 80%, 90%, or 100% of normal for the individual or for the species.

In preferred embodiments, either prior to or following the administration of the viscosity-increasing agent, the hematocrit of the mammal is decreased by at least 30%, 40%, 50%, 60%, 70%, 75%, or 80%.

In certain embodiments, the viscosity-increasing agent, solution, individual or patient, condition of the patient, and other selections or parameters are as specified for other aspects herein.

In another aspect, the invention provides a method for shifting the transfusion trigger threshold in a patient by administering to a patient suffering from a reduction in red blood cell concentration a pharmaceutically acceptable viscosity increasing agent in an amount sufficient to increase or maintain functional capillary density at at least 30% of normal or to increase plasma viscosity at least 25% or both. In general, the effect of the administration is to maintain acceptable tissue perfusion even at significantly lowered oxygen-carrying capacity of the blood. It is believed that tissue perfusion is maintained by maintaining or restoring capillary blood flow by preventing or reversing vasoconstriction of microscopic blood vessels and by increasing capillary pressure.

In certain embodiments, functional capillary density is increased to or maintained at least 30%, 40%, 50%, 60%, 70%, 80%, 90%, or 100% of normal. In certain embodiments, plasma viscosity is increased at least 25%, 30%, 35%, 40%, 50%, 60%, 70%, 80%, 90%, 100%, or even more.

In preferred embodiments, the reduction in red blood cell concentration is at least 40% from normal. Preferably the reduction is at least 50%, 60%, 70%, 75%, or 80% from normal. The reduction can be due to various mechanisms, but is commonly due to hemodilution as a result of the use of any of a variety of plasma expanders, or is due to pathologic reduction in red blood cells.

In preferred embodiments, the patient is a large mammal, preferably a human.

In preferred embodiments, transfusion trigger is shifted down by at least 10%, preferably by at least 20%, and more preferably by at least 30%, 40%, or even 50% or more from the transfusion trigger with isovolemic hemodilution using a low viscosity plasma expander such as saline or Ringer's lactate.

In connection with the medical advisability of performing a blood transfusion, the term "transfusion trigger" or "transfusion trigger threshold" refers to the conditions at which it becomes clinically recommended to perform a blood transfusion to maintain perfusion and oxygenation of tissues. Using the present invention, it is possible to maintain both microcirculation and sufficient oxygenation at lower hematocrit levels than when plasma viscosity is lower. The trigger level can vary depending on the subject species.

In connection with the circulatory system of a mammal, the term "microscopic blood vessels" or "microcirculation"

refers to small blood vessels which are generally 125 μm or less in diameter (normally dilated inside diameter), preferably 100 μm or less, and specifically includes those blood vessels which are too small to see with the naked eye.

In yet another aspect, the invention provides a method for treating a patient suffering or at risk of a condition characterized by a reduction in peripheral blood flow by administering to the patient a pharmaceutically acceptable viscosity increasing agent. Preferably this method is used in cases where the patient's blood has undergone hemodilution, such that the hematocrit is reduced, preferably reduced to a level which is in the range of 40% to 80% reduction from normal for the species, more preferably in the range of 50% to 80% reduction, still more preferably in the range of 50% to 75% reduction. The viscosity-increasing agent is administered in an amount sufficient to maintain or increase peripheral blood flow at a level at least 30% of normal, preferably at least 40%, 50%, 60%, 70%, 80%, 90%, or 100% of normal under conditions where the peripheral blood flow is decreased or would decrease below that level in the absence of administration of the agent or other treatment to maintain or increase peripheral blood flow.

Various embodiments involve the selections as described for other aspects herein, e.g., for mammals, specific parameters of the viscosity-increasing agent or solution, increases in viscosity, increases in capillary flow, and others.

In another aspect, the invention provides a method for treating a patient or preserving a tissue, by performing a hemodilution and in conjunction, preferably simultaneously or subsequently, administering a pharmaceutically acceptable viscosity-increasing agent as described. This method is particularly applicable where it is desired to maintain or increase microvascular flow, but where hemodilution has not yet occurred.

Certain embodiments of this aspect involve selections or parameters as described for other aspects herein, e.g., for mammals, specific parameters of the viscosity-increasing agent or solution, increases in viscosity, increases in capillary flow, and others.

In another aspect, the invention provides a method for enhancing or maintaining the release of vasodilators and shear stress dependent vasodilators in the system of microscopic blood vessels of a mammal by administering to the mammal a pharmaceutically acceptable viscosity increasing agent in an amount sufficient to increase or maintain microvascular blood viscosity under conditions where, in the absence of said viscosity-increasing agent or other treatment which maintains or increases microvascular function, microvascular function would be reduced. Shear stress dependent vasodilators are known to those skilled in the art, and include prostacyclin and nitric oxide (NO).

Preferred embodiments are as described for other aspects herein, e.g., for mammals, specific parameters of the viscosity-increasing agent or solution, increases in viscosity, increases in capillary flow, the level of maintenance or enhancement of microcirculatory flow (capillary flow) and others.

In another aspect, the invention provides a method for determining the amount of a viscosity-increasing agent for administration to a mammal, whereby microvascular circulation is increased or maintained. The method involves calculating the amount of viscosity-increasing agent solution which will produce a desired plasma viscosity in a particular patient or class of patient, e.g., in a particular species. Alternatively, the calculation can be based on the amount of viscosity-increasing agent needed to produce a desired blood viscosity in a particular patient. The method can also include selecting or obtaining a quantity of the viscosity-increasing agent or solution. The method can also include selecting an individual for administration of the solution; the individual may have or be at risk of hemodilution which would impair microvascular function in the absence of a transfusion or administration of a viscosity-increasing agent solution, or may be a subject for intentional hemodilution, e.g., as described for particular conditions or procedures herein.

In another aspect, the invention provides a method for enhancing the biological function of a hemoglobin-based artificial blood product or plasma expander that provides insufficient viscosity to maintain sufficient wall shear stress by administering to a patient a viscosity increasing agent of the present invention in conjunction with the hemoglobin-based artificial blood product or plasma expander in am amount sufficient to elevate plasma viscosity sufficiently to maintain functional capillary density in a mammalian patient at least 30% of normal, preferably at least 40%, 50%, 60%, 70%, 80%, 90%, or 100% of normal.

In preferred embodiments, the patient, patient condition, viscosity-increasing agent, and composition or other selections are as described for other aspects herein.

The term "in conjunction" means that the blood product and the plasma expander will be present in the individual together with timing such that both will be present in effective concentrations in the body together. Preferably the two products will be administered at the same time, either by combining the products before infusing or by infusing at the same time, where the "same time" means clinically the same, i.e., one infusion is started, and then the other is started as soon as practical, e.g., within 5, 10, 15, or 20 minutes after the first infusion is begun and medical personnel have confirmed that the first infusion is operating properly. Alternatively, either product may be infused before the other, or the infusion of one may begin before the other but overlap in time (e.g., overlap for at least ¼, ⅓, ½, ⅔, or ¾ of the infusion time of the shorter infusion time of the two products. Where one product is infused before the other, a medical practitioner of ordinary skill will understand which product to begin first, how close in time the products should be administered, and the appropriate quantities to use, in order to provide the desired or required effects.

The term "hemoglobin-based" means that oxygen-carrying function in the artificial blood product is provided by hemoglobin or a hemoglobin derivative.

In still another aspect, the invention provides a packaged solution comprising a viscosity-increasing agent, where the solution is in a container. Preferably the solution consists essentially of the viscosity increasing agent in an aqueous solution or in powder form (e.g., to be reconstituted for use). In preferred embodiments the solution has a viscosity as described for preferred embodiments of other aspects of the invention. Likewise, in preferred embodiments, the viscosity-increasing agent is as described herein. The container may be any of various types, e.g., as commonly used in connection with liquid blood products and/or plasma expanders. Examples include glass bottles and bags of an acceptable plastic. An acceptable plastic is one chemically compatible with the solution, and which is also suitable according to conventional standards for containing solutions for internal administration in a mammal, preferably for direct injection into blood vessels. The solution container will maintain the solution in a sterile condition prior to use of the solution and preferably during administration of the solution. Preferably the solution is approved for a particular use or uses by a regulatory authority which reviews and approves such products, e.g., by the U.S. Food and Drug Administration. Preferably both the solution and the packaging are so approved. Preferably the solution is approved for direct injection into the bloodstream of a mammal, preferably a human. Preferably the package also includes a package insert or other format providing information on approved use. In preferred embodiments, the container is a glass or plastic bottle or a plastic bag containing 50 ml±10%, 100 ml±10%, 200 ml±10%, 500 ml±10%, or 1000 ml±10%. In other embodiments, the container contains a volume of 50 to 250 ml, or 100 to 300 ml, or 200 to 500 ml, or 400 to 700 ml, or 600 to 100 ml. In preferred embodiments, the packaged solution also includes one or more other components of those commonly utilized in connection with the sterile administration of blood products or other intravenous or intraarterial liquid administration, such as tubing (at least internally sterile), clamps, fittings for insertion or connection of needles, sterile needles, and/or sterile coverings.

In certain embodiments, the viscosity-increasing agent is as described herein and/or the viscosity of the solution is as described herein.

In another aspect, the invention provides a pharmaceutical composition which contains at least one pharmaceutically acceptable viscosity increasing agent and a pharmaceutically acceptable carrier. In preferred embodiments, the composition has a viscosity of 3 to 30 cp, 5 to 25 cp, 7 to 20 cp, 8 to 18 cp, 10 to 17 cp, or 12 to 15 cp, and is suitable for injection into the bloodstream of a mammal.

In preferred embodiments, the viscosity-increasing agent is or contains a polyethylene glycol-dextran (PEG-dextran) conjugate. The PEG of said PEG-dextran conjugate preferably has an average molecular weight of between 1,000 and 40,000, or between 2,000 and 40,000, or 2,000 and 30,000, or 3,000 and 30,000, or 5,000 and 30,000, or 5,000 and 20,000, or 10,000 and 40,000, or 10,000 and 30,000 or 10,000 and 20,000, or 20,000 and 40,000, or 20,000 and 30,000. Other preferred size ranges include any range described by taking a size as just listed and assigning that value as the lower range limit and another larger size as just listed and assigning that value as the upper range limit. The dextran portion of the conjugate preferably has an average molecular weight of between 5,000 and 500,000 daltons, or between 10,000 and 500,000, or between 20,000 and 400,000 or 20,000 and 300,000 daltons, more preferably between 30,000 and 200,000 daltons, still more preferably between 50,000 and 150,000 daltons, and most preferably between 60,000 and 100,000 daltons. As with the PEG portions, additional preferred ranges are described by taking any of the values specified and using that value as the lower limit of the size range and taking a second, larger value as just listed as the upper limit of the range. The number of PEG moieties attached to each dextran molecule can be varied as desired to control the properties of the conjugate. Alternatively, the agent is one of those listed below, or others known or developed in the art.

It is highly preferred that the composition is approved for injection into a mammal, preferably into dogs, cats, sheep, swine, horses, bovines, monkeys, chimpanzees, apes, or humans.

These compositions can be used in embodiments of the other aspects of the present invention.

The invention also provides a method for monitoring the clinical condition or stability of a patient or the need for a transfusion by determining the viscosity of the patient's blood or plasma. The determination can be performed by conventional means. The method can also include determining the hemoglobin concentration or hematocrit as a measure of the oxygen carrying capacity of the blood. As described herein, the viscosity, preferably in conjunction with the hematocrit (e.g., the level of hemodilution) is indicative of the need for medical intervention. Preferably the method includes using the determination or determinations as an indicator or indicators of the need or timing for performing a blood transfusion. The method preferably includes selecting a patient for monitoring who has undergone or is expected to undergo hemodilution or who is suffering from a condition or is undergoing or expected to undergo a treatment procedure in which hemodilution occurs or is expected to occur or be performed.

In preferred embodiments of the various aspects of the present invention, the viscosity-increasing agent is one of the following compounds which can also be used in combination:

1) high MW dextrans (e.g., of at least 70,000, 100,000, 150,000, 200,000, 350,000, 400,000, 450,000, or 500,000 daltons average molecular weight)
2) high MW starches and polymerized starches
3) N-linked glycans, Deoxy sugars, acidic sugars, hexosamines
4) polyvinylpyrrolidone
5) albumin and polymerized forms
6) ethylcellulose
7) dextran microspheres
8) gamma-globulin-polyvinylalcohol-dextrans
9) hydrogels w/dextran dialdehydes
10) polyethylene glycol modified dextrans
11) polyvinyl pyrrolidone (PVP) modified colloids such as dextrans, starches, and albumin There are also a significant number of new gelatin and biopolymers being manufactured which can be utilized in this invention. Other compounds as know to those skilled in the art may also be tested and used.

Preferably, a selected viscosity-increasing agent has a molecular weight in a range as specified in connection with dextrans above or as specified for other viscosity-increasing agents herein.

Generally the viscosity-increasing molecule or molecules will be formulated in a manner depending on the physical characteristics of the molecules as understood by those skilled in art. In most cases a formulation utilizing 5% dextrose in water (D5W), saline, or Ringers' lactate will be useful. Generally the solution will be in the pH range 3.0–7.0, preferably 4.0–7.0, and still more preferably 5.0–7.0.

For a particular application, materials and conditions should be avoided which cause levels of coagulation or red blood cell aggregation which would pose a medically unacceptable risk to the patient, e.g., by causing blood vessel occlusion, e.g., in the brain or heart. One skilled in the art would be familiar with selection of appropriate materials for a particular application and with verifying suitability.

In embodiments of the aspects of the invention relating to methods of maintaining or enhancing peripheral blood flow and other aspects of the invention, the solution containing a viscosity-increasing agent is used in connection with a patient or tissue condition in which maintenance or enhancement of capillary function (e.g., peripheral blood flow) is beneficial. In many cases, the solution will be used to lower the "transfusion trigger" in acute hemodilution. In addition, there are other potential indications, i.e., any condition in which plasma viscosity falls to, or is at risk of falling to below the level at which capillary flow is compromised, e.g., below about 2 cp or even 1.4–2.0 or 1.4–1.8 cp in humans.

In certain embodiments, the invention can be used to enhance delivery of blood, therapeutic or diagnostic agents into tumors by enhanced microcirculation. In certain cases, this will provide the ability to capitalize on enhanced oxygen delivery to hypoxic regions of tumors.

In another aspect the invention is also useful in organ preservation for transplant purposes. Maintaining organ perfusion by maintaining capillary perfusion and microvascular function using the solutions of this invention can greatly enhance the condition of many organs and/or allow the use of organs which otherwise would have deteriorated to a degree precluding transplantation use. Typically, the viscosity-increasing agent solution would be administered prior to harvest, either immediately before to preserve capillary condition during the harvest and storage or transport process, or earlier to preserve the condition of the organ during the period of terminal deterioration of the donor's condition.

In other embodiments, the solutions of the invention are also useful in the treatment of myocardial infarction in order to preserve microcapillary flow.

In other embodiments, the solutions of the present invention are useful in sickle cell crisis in order to maximize microcirculatory blood flow.

The solutions are also useful in connection with shock, which can be, for example, hypovolemic, hypotensive, septic, or neurogenic shock.

The solutions are also useful in connection with a wide range of surgical procedures, e.g., for pre-, per- and post-operative plasma and blood replacement. For example, the solutions can be used in vascular and plastic surgery to improve local circulation and decrease the risk of thromboembolism. The solutions can also be used in open heart surgery, e.g., in connection with volume replacement and/or as an additive to a perfusate of a heart-lung machine.

Likewise, the solutions are advantageous for hypovolemic prophylaxis during regional anesthesia, such as epidural or spinal anesthesia.

The solutions can also be used for prevention of early graft failure via improvement in blood flow. This can, for example, prevent ischemia-reperfusion injury. Similarly, the solutions can reduce the risk of necrosis in critical ischemic conditions such as limb salvage or amputations or crush injuries.

In addition, the solutions can be used in treatment of conditions such as acute ascites or lymphedema or adult respiratory distress syndrome (ARDS).

The solutions can also be beneficial in the treatment of burns to maintain microcirculation in viable tissues.

Maintenance of microcirculation using the present invention is also beneficial in the treatment of embolisms, such as fat or thromboembolic embolisms, such as pulmonary, venous, cerebral embolisms.

The invention is also useful in the treatment of other conditions, which can, for example, include chronic ulceration, acute vascular infarction (e.g., cerebral or peripheral), pancreatitis, peritonitis, paralytic ileus, traumatic and idiopathic hearing loss, gangrene, and Raynaud's disease. As indicated above, the invention is not limited to use in connection with the specifically listed conditions or applications.

In most cases, the solutions of the present invention will be used in cases where the hematocrit of an individual in decreased (i.e., hemodilution), either as a result of a disease or condition, or by deliberate intervention. In the case of the indications or applications listed above, certain situations will generally involve hemodilution not deliberately connected with the administration of a viscosity-increasing agent or solution of this invention. For example, hemodilution will commonly be present in cases of shock, in connection with surgery, in connection with hypovolemic prophylaxis during regional anesthesia, and in connection with serious burns, as well as in other cases involving the administration of low viscosity plasma expanders or artificial blood products.

In other situations, it can be beneficial to create hemodilution (e.g., by exchanging blood with a plasma expander, in connection with the administration of the present viscosity-increasing agents. These situations can often include prevention of graft failure, prevention of ischemic-reperfusion injury, reducing risk in critical ischemic conditions, in treatment of acute ascites, lymphedema, or ARDS, in connection with treatment of embolisms, chronic ulceration, pancreatitis, peritonitis, paralytic ileus, traumatic and idiopathic hearing loss, gangrene, or Raynaud's disease, and in vascular and plastic surgery. For example, in surgery, a portion of the patient's blood can be removed and replaced with a plasma expander as described for the present invention. In some cases, it can then be advantageous to retain the removed blood and replace it after the surgery.

In addition to the applications describe above, solutions of viscosity-increasing agents can be used in a process of small volume resuscitation using a hyperviscosity, hyper oncotic pressure solution. The small volume of hyperviscous, hyper oncotic pressure solution will draw fluid into the circulation from the tissues, simultaneously providing restoration of circulation volume and viscosity. Typically, the solution will have a viscosity in the range of 8 to 25 cp, preferably 10 to 20 cp, more preferably 12 to 20 cp. Typically, 100 to 700 ml would be used, preferably 200 to 600 ml, more preferably 250 to 500 ml, and most preferably 250 to 400 ml.

Small volume resuscitation as described would generally be particularly advantageous in cases where large volume resuscitation would be contraindicated, e.g., patient with fluid overload, such as with congestive heart failure/pulmonary edema or ascites.

In the aspects and embodiments of this invention describing methods that involve a patient or individual, the method can also include the selection of a patient or individual, preferably one who has hemodilution or loss of blood, or who is expected to be subjected to a hemodilution. In particular embodiments, the patient or individual is suffering from or subject to a disease or condition or procedure as specified herein.

In the various aspects described herein, when a range of values is described, the range includes the endpoints unless specifically stated to the contrary.

As used in the claims to describe the various inventive aspects and embodiments, "comprising" means including, but not limited to, whatever follows the word "comprising". Thus, use of the term "comprising" indicates that the listed elements are required or mandatory, but that other elements are optional and may or may not be present. By "consisting of" is meant including, and limited to, whatever follows the phrase "consisting of". Thus, the phrase "consisting of" indicates that the listed elements are required or mandatory and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they affect the activity or action of the listed elements.

Additional features and embodiments will be apparent from the following description of the preferred embodiment and from the claims.

BRIEF DESCRIPTION OF THE DRAWINGS

FIGS. 2A and 2B are graphs showing vascular tone vs. systemic hematocrit. Data are presented as means±S.D. ●, Dextran 70 exchange; ▼, Dextran 500 exchange. Broken line represents baseline level. *P<0.05. Baseline diameters ($\mu$m) in each animal group were as follows: level 1 [arterioles (A): 62.4±18.2; n=44, venules (V): 68.8±37.5, n=42]; level 2 (A; 57.9±17.8, n=46, V: 70.9±39.2, n=36); level 3 LV (A; 56.6±12.3, n=49, V: 78.5±29.9, n=37); level 3 HV (A; 57.4±15.3, n=47, V; 68.9±32.7 n=38). n, No. of vessels studied.

FIGS. 3A and 3B are graphs showing arieriolar and venular red blood cell (RBC) velocity vs. systemic hematocrit. Initial increase in arteriolar RBC velocity was followed by a return to baseline with HV protocol, whereas LV protocol led to a reduced RBC velocity. Similar pattern was observed in venular RBC velocity except the return to baseline levels was earlier, occurring after the second exchange. Data are presented as means±SD. ●, Dextran 70 exchange; ▼, Dextran 500 exchange. Broken line represents baseline level. *P<0.05. Baseline RBC velocities (mm/s) in each animal group were as follows: control (A: 4.9±3.8 V: 1.0±0.7); level 1 (A: 4.3±2.4, V: 1.2±0.8); level 2 (A: 4.5±2.5, V: 1.2±1.4); level 3 LV (A: 4.0±2.3, v; 1.0±0.8); level 3 HV (A: 4.1±2.7, V: 1.1±0.9).

FIGS. 4A and 4B are graphs showing arteriolar and venular blood flow vs. systemic hematocrit. Hemodilution led to initial increase in blood flow in both vessel types. At the level 3 exchange, HV protocol was able to maintain blood flow at baseline levels, whereas LV protocol resulted in reduction. Data are presented as means±SE relative to baseline levels. ●, Dextran 70 exchange; ▼, Dextran 500 exchange. Broken line represents baseline level. *P<0.05.

FIG. 5 is a graph showing the effect of hemodilution on capillary perfusion as a plot of functional capillary density vs. systemic hematocrit. Functional capillary density (FCD) was unchanged after level 1 exchange. Drop in FCD was greater after level 3 LV than level 3 HV exchange. Data points are means±SD relative to baseline. ●, Dextran 70 exchange; ▼, Dextran 500 exchange. *P<0.05. Baseline FCD ($cm^{-1}$) in each experimental group was as follows: level 1 (105.8±22.1); level 2 (121.2±20.9); level 3 LV (109.2±22.2); level 3 HV (107.6±22.3).

FIG. 6 is a set of bar graphs showing the distribution of microvascular $Po_2$ v. hemodilution level. A, arterioles; V, venules; T, tissue. Shift in arteriolar $Po_2$ to the right and venular $Po_2$ shift to the left, after level 1 and 2 exchange maintained tissue oxygenation at baseline levels. Level 3, extreme hemodilution, resulted in significant reduction across all categories. Both level 3 LV and level 3 HV caused a significant reduction in $Po_2$ in all categories. $Po_2$ measurements could only be made in vessels that had blood flow; thus, the histograms for level 3 LV do not include data from 2 animals that did not have blood flow in the tissue under study. Control group vessel diameters (means±SD, $\mu$m) were A: 57.0±18.5 (n=58), V: 69.9±35.3 (n=56), and RBC velocities (mm/s) were A: 4.9±3.8 (n=58), V: 1.0±0.7 (n=56). n, No. of vessels studied.

DETAILED DESCRIPTION OF THE PREFERRED EMBODIMENTS

Figure 1:
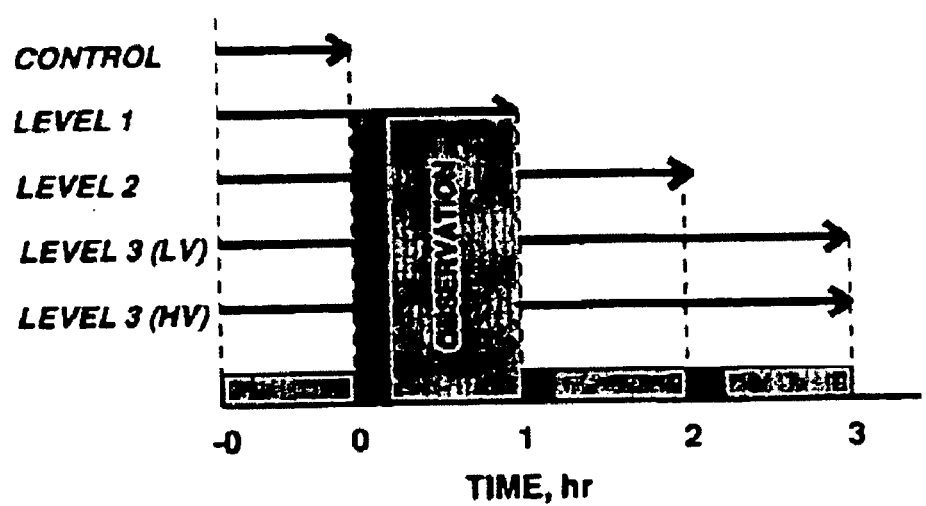
FIG. 1 is a histogram showing the time course of the experimental protocol for the hamster model system. Control/baseline characterization was performed before the exchange protocol. Progressive hemodilution was performed at the beginning of each hour and was followed by an observation period. Three levels of hemodilution were performed. Levels 1, 2, and 3 low viscosity (LV) were performed with Dextran 70. Level 3 high viscosity (HV) was performed with a combination of Dextran 70 and high-molecular-weight Dextran 500.

The present invention applies the principles and methods of engineering and life sciences toward understanding of the mechanisms that determine tissue oxygenation under normal conditions and when blood losses (i.e., decrease of the oxygen carrying capacity of blood due to the decrease of the number of red blood cells) are remedied by the introduction of plasma expanders. Advances in this field have led to the development of a new generation of plasma expanders that significant decreases the so called "transfusion trigger" or the concentration of hemoglobin (Hb) in blood at which medical practice indicates that a blood transfusion is necessary. With currently available therapies the present level of this threshold is at about 7 g Hb/dl, and lowering this by as little as 1 g Hb/dl could lead to blood savings in excess of 1 million units per year. The significance of these numbers can be appreciated by considering that The National Blood Data Resources Center predicts that in the year 2,000 Americans will donate about 11.7 million units of blood, while hospitals will need 11.9 million. Blood saving techniques and artificial blood are the two principal approaches contemplated and underway to remedy the shortfall in the blood supply, however blood saving techniques can at most postpone the inevitable blood shortfalls.

Artificial blood appears to be a logical solution, however the recent failure of Baxter Healthcare in completing phase III clinical trials with their human hemoglobin based product Hemeassit™ and their withdrawal from this area after expenditures in excess of 500 million dollars illustrates the difficulty of the problem. Three other artificial blood products based on free hemoglobin solutions are presently in clinical trials: Hemosol Inc. (Toronto) and Biopure (Cambridge) have a product with similar properties to Hemassist™ and cause hypertension, the same feature that caused the Baxter failure. Northfield (Chicago) has a product that has not been studied by independent groups. It is presumed not to be vasoactive, however it requires 3 units of human blood for making one unit of artificial blood, therefore it is not the solution of blood shortages, since it aggravates the problem. Furthermore none of these products has a half life in the circulation greater than 12 hours.

Rationale for Blood Transfusion: Volume vs. Oxygen Carrying Capacity Restoration In order to remedy the problem of blood shortages we addressed the fundamental question of what are the reasons for giving a blood transfusion. The immediate answer is that they are given to restore oxygen carrying capacity. However in many instances the most critical element is the restoration of blood volume. In fact, in emergencies the priority is to re-establish blood volume, which is done with plasma expanders, and secondly oxygen carrying capacity, which requires the transfusion of blood.

Therefore the remedy of blood losses contemplates a two-step approach, volume restitution being followed by oxygen carrying capacity restitution once the transfusion trigger is passed. This sequence and landmarks are the results of experience and the evidence that volume restitution with plasma expanders beyond the transfusion trigger present increasing risks, and is not effective. This is evident in the practice of hemodilution with colloidal plasma expanders which shows that the oxygen delivery capacity of the circulation falls below normal values once half of the red blood cells are lost.

Cardiovascular Function and Microscopic Transport

Extension of the volume restitution phase and postponement of the red blood cell restitution to a lower threshold of the current transfusion trigger requires a change of the properties of the presently used plasma expanders, since their present formulations are not adequate for insuring that tissue perfusion and oxygenation will be maintained within an acceptable margin of safety. Furthermore, in order to improve physical properties of biomaterials currently used as plasma expanders, it is critical to understand the function of the cardiovascular system during conditions in which hemoglobin levels are near or at the transfusion trigger.

An understanding of the possible manipulations of the properties of plasma expanders can be obtained by analyzing the mechanics of the basic functions of the cardiovascular system. Our approach was to establish how macroscopic blood fluid properties affect the endpoint of cardiovascular function, namely the microscopic supply of oxygen to the tissue and the extraction of the products of metabolism from the tissue. The conceptual analysis began with the delivery process involved in convecting required gases and solutes by blood, which subsequently diffuses into the cells, and the reverse process that takes place with the products of metabolism. While the final phase of both delivery and extraction is dominated by diffusion, a passive process, the convective process requires energy, and is actively regulated by several mechanisms whose goal is to insure the continues passage of blood through capillaries, so that moving fluid is contiguous to virtually every cell of the organism.

The rate of convection of blood is determined by the pressure imparted by the heart, the geometrical properties of the vasculature and the rheological properties of blood. The varying oxygen demand of the tissue as a whole and of each microscopic domain is regulated by "vascular tone" a term used to describe the state of contraction or dilatation of blood vessels. The active (and passive) variation of vessel diameter is a high gain regulator of blood flow because of the 4th power dependence of vascular hydraulic resistance on the vessel diameter. Blood viscosity is also a determinant of blood flow, however since blood composition (and therefore viscosity) is relatively constant throughout the life of the organism, it is generally considered to have a lesser role in regulating blood flow. Furthermore, in the normal organism, large variations of blood viscosity can be compensated by minute changes of vascular diameter.

Plasma Viscosity, Tone and Cellular Function

While the above considerations are valid when tone (vascular diameter) and blood viscosity are analyzed independently, present information shows that these factors are actually closely intertwined in controlling tissue perfusion and oxygenation, where shear stress generated by blood flowing over the endothelium is the linkage between the rheological properties of blood and vascular tone.

Shear stress is nearly uniform in the vasculature and generates vasoactive materials that directly affect vascular diameter, namely prostacyclin (Frangos et al., 1985, *Science* 227:1477–1479), NO (Frangos et al., 1985, *Science* 227:1477–1479; de Witt et al., 1997, *Phyugers Arch.* 434:354–361), and endothelin (Malek, 1999, *Biochem, Biophy. Res. Comm.* 254:231–142). Departures from normal level of shear stress affects the production of these materials and eventually leads to pathological conditions. Increased shear stress occurring at stenosis (vascular narrowing) is implicated in the formation of arteriosclerotic abnormalities. Lowered shear stress is identified with endothelial malfunctions that promote vasoconstriction (our studies), and apoptosis (Dimmeler, 1998, *Circ. Res.* 83:334–341, Deb et al., 1999, *J. Trauma* 46:582–589).

The relationship between blood flow Q (equivalent to tissue oxygenation in normal conditions), vessel diameter D, shear stress at the vessel wall $tau_w$, and blood viscosity $\mu$ can be readily obtained from basic fluid mechanic considerations as:

$$Q = pi\ D^3 tau_w / 2\mu \qquad (1)$$

where all parameters are interdependent through active mechanisms.

Blood Viscosity Distribution in the Cardiovasculature and Hemodilution

Blood viscosity changes significantly with changes in the concentration of red blood cells (hematocrit) because it is dependant on hematocrit squared. The loss of red blood cells in hemorrhage and the practice of hemodilution leads to important reductions of blood viscosity. Conversely adaptation to high altitude (low oxygen environments) leading to increased red blood cell concentration, significantly increases blood viscosity. It is established that the cardiovasculature adapts to departures from normal hematocrit and viscosity provided that this is within given limits (Richardson and Guyton, 1959, *Am J. Physiol.* 197:1167–1170), and it is generally assumed that it is beneficial for the organism to be exposed to blood viscosity that is lower than normal (Messmer, 1975, *Surg. Clins. N. Am.* 55:659–678).

The mechanisms responsible for the changes in hemodynamics following changes in blood viscosity have been primarily viewed as due to the changes in cardiac performance determined by the change in peripheral vascular resistance and cardiac filling demonstrated by Richardson and Guyton (supra). Little consideration has been given to the possibility that the vasculature per se may be affected by these changes.

Viscosity can be a significant effector of vascular diameter, when it leads to changes in shear stress, thereby affecting the release of vasoactive substances. Furthermore, changes of viscosity are not uniform throughout the circulation. The major mechanisms that change viscosity in the circulation are the change in plasma viscosity, the change of hematocrit, and the change of the tendency of red blood cells to aggregate. Of these mechanisms only the change of plasma viscosity provides an approximately uniform change in viscosity in the cardiovasculature. Conversely changing either hematocrit or blood agreggability leads to compartmentalized changes, and therefore shifts in the distribution of hydraulic pressure in the circulation.

The non-uniformity of red blood cell related viscosity changes is because red blood cell concentration and blood flow average shear rate are not uniform in the circulation. Hematocrit is approximately uniform and close to the systemic value in arterioles of up to about 50 $\mu$m diameter, and then decreases approximately uniformly as a function of diameter, being about half of the systemic value in capillaries. Furthermore, changes of hematocrit are proportional to the degree of dilution or concentration of red blood cells in the systemic vessels, but microvascular hematocrit changes have a lower gain than systemic changes, and microvascular hematocrit tends to remain approximately constant. As a consequence of this distribution of hematocrit in the circulation and hydrodynamic effects due to the presence of a cell free plasma layer, microvascular viscosity changes linearly as a function of changes of systemic hematocrit, while systemic blood viscosity changes in proportion to the systemic hematocrit squared. A similar situation is present in considering agreggability, since this phenomenon is shear rate dependant, causing the primary effects be present in the venular and venous circulation and mostly absent in the arterial, arteriolar and capillary circulation.

Re-distribution of Blood Pressure in the Microcirculation Due to Altered Viscosity As an example of redistribution of blood pressure in the microcirculation, consider the process of hemodilution, which significantly lowers systemic blood viscosity, but only linearly changes microvascular viscosity. In the absence of shear stress related effects, if the heart responds to the lowering of peripheral vascular resistance by increasing cardiac output, then viscous pressure losses are significantly smaller in the systemic circulation than in the microcirculation. Consequently a greater portion of mean arterial blood pressure is transmitted to the microcirculation, as predicted by modeling studies. (Mirhashemi et al., 1987, *Int. J. Microcirc.: Clin. Exp.* 6:359–370). This response takes place if viscosity and blood flow velocity combine so that shear stress is maintained. However, further lowering blood viscosity will eventually lower shear stress because the heart cannot increase cardiac output indefinitely, flow will be further restricted and minimal arterial pressure will be transmitted to the microcirculation.

Changes in microvascular pressure affects both the arterioles through the myogenic response (Johnson, 1986, *Circ. Res.* 59:483–495) and the capillaries, affecting the passage of red blood cells (Lindbom and Arfors, 1980, *Microvasc. Res* 19:197–208). An increase in arteriolar pressure causes vasoconstriction, which, according to our findings, also occurs with substantial reductions of blood viscosity which lead to the simultaneous reduction of vascular diameter and functional capillary density (capillaries with red blood cell transit) (Tsai et al., 1998, *Am. J. Physiol.* 275:H2170–H2180) and presumably capillary pressure. The reduction of functional capillary density following the reduction of arterial pressure has been demonstrated by Lindbom and Arfors. We have demonstrated the effect of reducing functional capillary density following vasoconstriction due to the introduction of free hemoglobin in the circulation, which is a potent vasoconstrictor due its NO scavenging properties.

Blood Viscosity and Functional Capillary Density

The significance of functional capillary density is that it is a critical microvascular parameter in survival during acute blood losses. In our hamster model subjected to 4-hr 40 mmHg hemorrhagic shock, it accurately predicts outcome, being zero in non-survivors and 50% in survivors (Kerger et al., 1996, *Am. J. Physiol.* 279:H827–H836). An adequate level of functional capillary density has a dual role. On one hand it provides a mean for delivering oxygen to the tissue, even though a substantial amount of oxygen leaves the microcirculation prior to blood arriving to the capillaries (Duling) (Intaglietta). Equally, or even more, important is its role in preventing the accumulation of byproducts of cellular metabolism by providing a route for their extraction. Finally, the capillary system provides the largest surface area in the circulation and the highest level of shear stress.

In addition, shear stress and tissue oxygenation are linked on and beyond the regulation of hemodynamics via the control of vascular tone, given the findings that adequate levels of NO are necessary for the regulation of mitochondrial oxygen consumption (Shen).

These considerations indicate that vascular tone and blood viscosity are linked in a complex fashion. This complexity provides an opportunity for introducing perturbations in the circulation that are highly beneficial for microscopic tissue perfusion. For instance, it is possible to hemodilute blood with a fluid whose viscosity is higher than that of plasma, in such a fashion that systemic blood viscosity is reduced, due to its dependence on squared hematocrit, while microvascular viscosity is increased, causing the increase of capillary pressure and the corresponding increase of functional capillary density.

Tissue Oxygenation, Vascular Tone, Plasma Expanders Viscosity and Transfusion Trigger Taken as a whole, the preceding analysis leads to the conclusion that the failure of conventional plasma expanders in insuring tissue perfusion, oxygenation and the extraction of tissue metabolites when they are used beyond the transfusion trigger is because the transfusion trigger is also is also a blood viscosity threshold. In other words, when human blood falls below 7 g/dl hemoglobin concentration, the concentration of red blood cells is too low to provide adequate viscosity in the microcirculation, leading to a condition of reduced shear stress, capillary collapse, and microvascular/endothelial/molecular dysfunctions. The levels of safety determined by intrinsic blood oxygen carrying capacity have not previously been tested independently from the failure of microvascular function inherent to low viscosity perfusion following dilution of red blood cells with conventional plasma expanders beyond the transfusion trigger. We further conclude that the level of oxygen carrying capacity required to safely oxygenate the tissue is much lower than that dictated by prior medical experience, so long as microvascular function is maintained.

Given these conclusions, we investigated the relationship between blood viscosity and vessel wall shears and tissue oxygenation, and determined how perturbations of systemic blood viscosity affect tissue oxygenation and acid base balance. Our goal was to delineate the relation between blood viscosity and blood oxygen carrying capacity (hematocrit) that provides normal microvascular function and tissue conditions for minimal hematocrit conditions. We propose to establish a new definition of the transfusion trigger based on the conditions that determine the threshold level microvascular function required for tissue survival, that stipulates blood hemoglobin content and blood viscosity. Finally, we provide examples of plasma expanders that can be used beyond the presently set transfusion trigger, and thus lower the need for blood transfusions.

Distribution of Hematocrit, Blood Viscosity, and Vascular Resistance in the Circulation Actual microvessel hematocrit $H_{micr}$ (value obtained by stopping flow and measuring the red blood cell concentration in a vessel) is lower than systemic. Cinephotometric measurements show that in the rabbit omentum capillaries hematocrit (Htc) falls to 45% of systemic values (Schmid Schönbein & Zweifach, 1975). Similar results were found in the cat (Lipowsky et al., 1980), the rat (Kanzow et al., 1982), the hamster cheek pouch (Sarelius and Duling, 1982), and cremaster muscle (Klitzman and Johnson, 1980). In arterioles of 60–70 $\mu$m diameter, the hematocrit is about 0.7 of systemic when the results of the referred studies are taken as whole. It should be noted that $H_{micr}$ is not indicative of red blood cell flux. This is conserved by the discharge hematocrit which is the value obtained by collecting the outflow from a blood vessel (Lipowsky, 1987). The presence of a layer of glycocans on the endothelial surface has also been proposed to be responsible for the apparent low hematocrits in the capillaries and the smaller arterioles.

As hematocrit decreases so does blood viscosity, however the regimes are very different for bulk blood, as present in the larger vessels, and the microvessels. For arterioles in the range of 47 to 24 μm diameter. Lipowsky et al., 1980, report that apparent viscosity η determined from in vitro and in vivo data for hematocrit in the range 0–36% is given by the relationship:

$$\eta = \eta_{plsma} + 0.0722 \, Htc \, (\eta, cp; Htc, \%; \eta_{plsma} \sim 1.2 \, cp) \quad (2)$$

In arterial and venous blood vessels, diameter>100 μm, blood viscosity is approximately proportional to Htc squared according to:

$$\eta = \eta_{plsma} + 0.0016 \, Htc^2 \, (\eta, cp; Htc, \%) \quad (3)$$

The actual blood pressure viscous losses as a function of vessel diameter are In variable from tissue to tissue. Lipowsky, 1987, reports that blood pressure in arterioles of about 60 μm diameter is about 80% of mean arterial blood pressure (MAP) in the cat mesentery and tenuissimus muscle, while the same vessels exhibit about 50% of MAP in the rabbit omentum and the spinotrapezious muscle. Thus we may assume that on the average in the circulation 30% of MAP is dissipated upon blood arriving to 60 μm arterioles, which defines $X_{art}$ the fraction vascular resistance attributable due to the arterial circulation. In most species, organs and tissues capillary pressure is specific pressure boundary condition, since it is controlled so that fluid exchange between blood and tissue compartments is in equilibrium. This requires that blood plasma colloid osmotic pressure and capillary pressure be approximately equal. The average capillary pressure that yields this balance is of the order of 25 mmHg (intaglietta and Zweifach, 1973), which indicates that if MAP is 100 mmHg, 75% of MAP is dissipated upon blood arriving to the capillaries. About 30% of arterial blood pressure viscous losses occur in blood vessels where viscosity depend on hematocrit squared ($X_{art}$=0.30), and 45% are due to the linear hematocrit dependence regime, which defines the microvascular fraction of microvascular resistance or $X_{micro}$=0.45. The remaining fraction, $X_{ven}$=0.25, defines the venous resistance.

Change in Vascular Resistance Following Hemodilution

Reducing hematocrit by 50% by isovolemic hemodilution does not change MAP, thus application of equations 2 and 3, for constant MAP and geometrical features of the vascular network (i.e., there are no vasoactive responses) shows that cardiac output must increase by 85%. Furthermore, viscous losses in the arterial circulation are lowered, those in the microvascular system are increased and capillary pressure is slightly decreased as shown in FIG. 1. Microvascular studies show that there are no major geometrical or systemic changes up to 50% hemodilution.

Hemodiluting blood to hematocrit 11% causes changes that cannot be predicted mathematically, because the vascular network exhibits a non-linear response where the relationship between vasoconstriction, lowered cardiac output, and lowered MAP can only be found experimentally. Functional capillary density falls to below 40% of normal when blood is hemodiluted to 11% hematocrit (Tsai et al., 1998) indicating that capillary pressure must be about half of normal according to the study of Lindbom and Arfors. If we assume that capillary pressure is about 50% of normal, we can compute the relative distribution of arterial and microvascular losses, and determine that vascular resistance, independently of viscosity has increased by about 170% (i.e., it is 2.7× normal). This is globally supported by the findings shown in FIG. 2.

Given that at 50% hemodilution, systemic and microvascular conditions are normal, we can determine what is the plasma viscosity $\eta_x$ needed for obtaining a blood viscosity that reproduces the hemodynamic conditions at 50% hemodilution (i.e., the limit of the linear range in hemodynamic responses to changes in blood viscosity). This can found by making a pressure balance equation, where the total arterial pressure is equal to the sum of arterial, microvascular and venous losses, under the assumption that the circulation has the same behavior relative to blood viscosity regardless of the relative contribution of plasma viscosity and red blood cell concentration, in the different compartments. This relationship is:

$$MAP = Q[(+0.0016 \, Htc^2)X_{art} + (\eta_x + 0.0733 Htc)X_{micro} + (\eta_x + 0.0016 \, Htc^2)X_{ven}] \quad (4)$$

where Q is the normalized blood flow relative to normal, and $X_{art}$, $X_{micro}$ and $X_{ven}$ are the fractions of total vascular resistance at the arterial, microvascular and venous compartments that delineate the hematocrit squared dependence vs. linear dependence of viscosity. Solving in (4) we obtain $\eta_x$=1.9 cp, which compares favorably with the value of 2.2 cp found in the experiments of Tsai et al., 1998.

Capillary Pressure and Functional Capillary Density

Equation (4) also provides an experimental handle with which to verify the different assumptions since each of its terms is a pressure dissipation terms, and the last term provides an indication of capillary pressure $P_c$, which can be measured directly, or:

$$P_c = Q(\eta plasma + 0.0016 \, Htc^2)X_{ven} \quad (5)$$

It is apparent that our derivation is a simplified representation of the events that take place once viscosity is lowered to the point that the vasculature responses are no longer linear, however our results allow to obtain an approximate analytical prediction of the consequences of changing plasma viscosity to cause the circulation to remain in its linear behavior, where vascular resistance, cardiac output and MAP adjust themselves so that capillary pressure remains approximately constant.

The relationship between capillary diameter and capillary pressure is still imperfectly understood. In the 60's Fung, Zweifach and Intaglietta (Fung et al., 1970, *Circ. Res.* 19:441–461) made torsion experiments in the mammalian mesenteric membrane and concluded that the capillary pressure diameter results of Baez showing that capillaries were relatively non-distensible, could be explained if their mechanical properties were derived from the tissue matrix rather that the capillary structure. This led to the conclusion that capillaries were tunnels in the tissue rather than tubes, and their mechanical properties derived from the tissue, rather than the capillary wall (Intaglietta & dePlomb, 1973, *Microvascl. Res.* 6:153–168).

These studies may be responsible for the prevailing perception that capillaries are rigid structures. However these studies did not test the physics of capillary decompression. The latter has only been studied indirectly through the effect that capillary diameter has on red blood cell passage. Mathematical modeling studies by Secomb et al. (*Prog. Appl. Microcirc.* 12:205–211) have shown that once capillary diameter reduces to 2.8 μm diameter red blood cells cannot deform further and do not pass through a capillary. Lindbom and Arfors lowered femoral artery pressure in the hind limb of the rabbit and found that the number of capillaries with red blood cell passage decreased in proportion to the reduction of pressure, being about 30% of normal when pressure in the femoral artery was 25 mmHg.

Reduced functional capillary density has not been studied directly in relation to capillary pressure. However, in conditions that lead to reduced capillary pressure there is invariably evidence of decreased FCD. This is apparent in hemorrhagic shock, where the reduction of functional capillary density was found to be due to endothelial swelling (Mazzoni et al., 1990, *Ann. Emerg. Med.* 19:350–358). In our own studies we have consistently found that the application of vasoconstrictors that reduce nitric oxide (NO) availability such as free hemoglobin solutions and L-NAME cause the reduction of FCD. Whether a non-functional capillary remains open to the passage of plasma, or it is occluded by red blood cells or leukocytes is not well established and may be random. However the strong correlation between survival in shock and FCD and acid base balance suggests that non functioning capillaries are occluded to the passage of plasma, a concept supported also from evidence obtained when infusing fluorescent markers in the circulation which in general do not appear in the occluded capillaries.

Our studies in the hamster model show that extreme hemodilution (Htc is 20% of control) with dextran 70 kDa, causes hypotension and FCD drops to near pathological values (Tsai et al., 1998). This is prevented by increasing plasma viscosity so that the diluted blood has a systemic viscosity of about 2.8 cp, which was achieved by infusing dextran 500 kDa. Thus high viscosity plasma can be an alternative to the use of blood for maintaining MAP and an adequate level of FCD.

FIG. 2 shows the computation of vascular resistance (inverse of vascular diameter) for the circulation applying Poiseuille's law to data on blood flow, MAP and blood viscosity in our hamster model for blood dilutions with Ringer's lactate and dextran 70 kDa. When blood viscosity is lowered to 2 cp, FCD is no longer maintained and vascular diameter decreases.

Low vs. High Plasma Viscosity Perfusion

In acute conditions, decreased Htc is considered harmless until the transfusion trigger is reached. The reduction of Htc with a crystalloid or colloidal plasma expander tends to equalize blood viscosity throughout the circulation, exposing the vasculature to low blood viscosity when conventional plasma expanders are used to maintain blood volume. There appears to be no well-defined benefit to lowering blood viscosity, excepting when it is pathologically high, and lowering blood viscosity through hemodilution is considered to have no adverse effects. Richardson and Guyton, 1959, determined that changes in blood viscosity are accompanied by compensatory changes in cardiac output, which compensate for changes in intrinsic oxygen carrying capacity of blood due to changes in Htc. This was confirmed systemically (Messmer, 1975) and in the microcirculation (Mirhashemi et al., 1988, Tsai et al., 1991, *Int. J. Microcirc.: Clin. Exp.* 10:317–334). Practice sets the transfusion trigger at 7 g Hb/dl, Htc~22%. The literature supports the concept that high viscosity plasma is either beneficial, or has no adverse effects in conditions of extreme hemodilution. Waschke et al., 1994 (*J. Cerebral Blood Flow and Metab.* 14:871–876) found that cerebral perfusion is not changed when blood is replaced with fluids of the same intrinsic oxygen carrying capacity over a range of viscosities varying from 1.4 cp to 7.7 cp. Krieter et al., 1995 (*Acta Anaest. Scad.* 39:236–244) varied the viscosity of plasma by adding dextran 500 kDa and found that medians in tissue $pO_2$ in skeletal muscle were maximal at a plasma viscosity of 3 cp, while for liver the maximum occurred at 2 cp. In general they found that up to a 3-fold increase in blood plasma viscosity had no effect on tissue oxygenation and organ perfusion when blood was hemodiluted, de Witt et al., 1997 found elevation of plasma viscosity causes sustained NO-mediated dilation in the hamster muscle microcirculation.

High viscosity plasma restores MAP in hypotension without vasoconstriction. Furthermore the shift of pressure and pressure gradients from the systemic to the peripheral circulation increases microvascular blood flow, which, in combination with increased plasma viscosity, maintains shear stress in the microcirculation, needed for the shear stress dependant NO and prostaglandin release from the endothelium (Frangos et al., 1985), and to maintain FCD. Conversely, reduced blood viscosity decreases shear stress and the release of vasodilators, causing vasoconstriction, offsetting any benefit of reducing the theological component of vascular resistance. Since resistance depends on the $4^{th}$ power of vascular radius and the $1^{st}$ power of blood viscosity, there are situations in which the effect of reducing blood viscosity with a low viscosity plasma expander reduces oxygen delivery to the tissue.

Molecular and Gene Expression Effects Due to Low Viscosity Reperfusion

Tissue perfusion with reduced blood viscosity can be deleterious at the cellular/endothelial level. Genes are activated following changes in the mechanical environment of cells and the endothelium uniquely responds to changes in its mechanical and oxygen environment according to programmed genetic schemes. Among these responses is the mechanism for self destruction, apoptosis, activated through a genetically controlled suicide process that eliminates cells no longer needed or excessively damaged.

Maintained blood viscosity or increased plasma viscosity in reperfusion is beneficial because basal levels of shear stress are necessary for the upregulation of superoxide dismutase (SOD) and NO which act as brakes to the inherent apoptotic capacity of endothelial cells (Dimmeler et al., 1998). Shear stress mitigates apoptosis due to oxidative stresses caused by $H_2O_2$ (Hermann et al., 1997, *Arterioscler. Thromb. Vasc. Biol.* 17:3588–3592). Increased shear stress leads to increased or normalized NO production. Shear stress dependant upregulation of Cu/Zn SOD and NO synthease blocks activation of the caspase cascade in response to TNF-α and oxygen radicals (Dimmeler et al., 1999, *Arterioscler. Thromb. Vasc. Biol.* 19:656–664). Thus, the production of Cu/Zn SOD and NOS by shear stress constitutes an important cellular mechanism for the preservation of the integrity of the endothelium. Furthermore, shear stress leads to NO induced vasodilation (de Witt et al., 1997) as well as the suppression of endothelin-1 gene expression (Malek et al., 1999). Therefore normal shear stress levels are necessary for lowering peripheral vascular resistance through the release of vasodilators (Frangos et al.,) and via gene expression mediated mechanisms.

Cell culture experiments show that interference with NO production is an apoptotic stimulus (Shen et al., 1998) which is directly mediated by shear stress upregulation of SOD and NO synthase (Dimmeler et al., 1999, *Arterioscler. Thromb. Vasc. Biol.* 19:656–664). Therefore, there is a direct link between reperfusion with low viscosity blood and the potential for apoptotic endothelial impairment, as per the report that reperfusion with Ringer's lactate caused an immediate 5-fold increase in apoptotic index of the bowel and mucosa walls relative to blood and dextran reperfusion (Deb et al., 1999).

Normalization of NO production lowers oxygen requirement of the endothelium and parenchymal tissue (Xie et al., 1996, *Circ. Res.* 79:381–387). Thus, normalized blood viscosity or increased plasma viscosity is not only beneficial via the transferral of pressure to the microcirculation and improvement of microvascular flow and FCD, but also because of the mitigation or prevention of long term (hours to days) endothelial damage triggered by programmed gene expression, and lowered potential damage due to hypoxia by lowering the tissue oxygen demand.

Concept & Rationale

Thus, a basic concept relevant to the present invention is that the presently accepted transfusion trigger demarcates the limit for the preservation of microvascular function, and not the limit for oxygen delivery capacity, when oxygen carrying capacity is reduced by the decrease of red blood cell concentration. A key factor in the maintenance of microvascular function is the maintenance of functional capillary density, a condition that requires normal capillary pressure. Thus, the transfusion trigger represents the limit for blood viscosity reductions that sustain normal capillary pressure. Furthermore, if blood viscosity is reduced by lowering the concentration of red blood cells, the required physiological effects derived from the presence of normal blood viscosity can be obtained by increasing plasma viscosity. As a result, there is a hemoglobin (hematocrit) region below the transfusion trigger, tentatively set in the 4.0 to 7.0 g Hb/dl range (for humans), where the organism functions normally and safely if microvascular function (FCD) is maintained. In this hemoglobin gap, the critical issue is maintenance of microvascular function, and not the intrinsic oxygen carrying capacity of blood.

Therefore, maintenance of blood viscosity above a specific threshold is necessary for maintaining the circulation within its linear range of adaptation to changes of blood viscosity and oxygen carrying capacity. When the circulation operates within its linear range, shear stress at the vascular wall, tissue oxygenation and the extraction of the products of metabolism is maintained to insure the adequate survival of the tissue. Maintenance of blood viscosity in the hemoglobin gap also prevents cellular damage derived from low shear stress conditions, and maintenance of microvascular function insured by the appropriately formulated plasma expander viscosity effectively offsets potential perturbations that may be caused by the lower oxygen carrying capacity of blood.

Specific Aims

As explained above, our objective was to utilize engineering analysis of the phenomena that take place when blood viscosity is changed, coupled with experimentation in the life sciences, particularly the microcirculation, to provide a fundamental basis for the economical design and production of a new type of plasma expander that will maintain microvascular function once the presently used transfusion trigger is passed. The use of this plasma expander lowers the transfusion trigger and thus can result in a significant decrease in the demand for blood transfusions.

To accomplish our objective we characterized microvascular hemodynamics in terms of blood pressure, blood flow, blood viscosity, vessel wall shear stress and blood $pO_2$ distribution in normal conditions, when hematocrit has been reduced by half (the transfusion trigger), and by ¾.

We can predict by calculation and modeling the change in plasma viscosity needed to restore the hemodynamic conditions present at the conventional transfusion trigger (hematocrit~22%, hemoglobin 7 g/dl). Upon verifying experimentally the minimal plasma viscosity increase required to maintain functional capillary density, we can augment the hematocrit (and decrease plasma viscosity) to attain a tissue $pO_2$ that is about 50% of normal. We can use tissue $pO_2$ to define simultaneously the new transfusion trigger, the required plasma and blood viscosity for the circulating blood, and the formulation of the volume replacement fluid to be infused once the current transfusion trigger is passed. The efficacy of the new formulation can be confirmed by subjecting an experimental model to hemorrhagic shock resuscitation modalities, including experiments with animals that have been tranfuse-exchanged and resuscitated with the newly formulated plasma expander.

For most applications, we design our plasma expander so that its osmotic and oncotic pressures are similar to those of natural plasma. The appropriate viscosity and oncotic pressure will be obtained by using mixtures of molecular weight fractions of a specific colloid.e.g., dextrans and HES-starches.

Thus, the plasma expander provides adequate and safe tissue perfusion and oxygenation when the hemoglobin content of blood is significantly lower than that embodied in the presently accepted transfusion trigger.

Using the animal model of the hamster skin fold and the rat mesentery, we reduced Htc to 50% and 25% of the normal value by isovolemic hemodilution. We used plasma expanders of low and high viscosity, so that blood viscosity is significantly lower than normal, and close to normal, to test the idea that maintenance of blood viscosity above a given threshold is necessary for maintaining FCD and preventing endothelial damage, and that significantly lower blood viscosity compromises microvascular viability. We found that high viscosity plasma expanders are beneficial because they maintain pressure and shear stress in the microcirculation.

In testing our ideas we performed the following:

1: Measured blood flow, blood pressure distribution, shear stress distribution, intra and extravascular oxygen distribution ($pO_2$) and FCD during reduced Htc by inducing isovolemic-isooncotic hemodilution (50% of control and 75% of control) with a low and high viscosity plasma expander (Ringers's lactate Dextran 70 & 500 kDa dextran) causing bulk blood viscosity (as measured in capillary viscometer at 100 sect average shear rate) to be 1.8–2.2 cp, and 2.8–3.2 cp respectively when Htc is 25% of control.

2: Formulated plasma expander of different viscosity through the mixture of fractions of different molecular weights of dextrans and HES starches. Tested these fractions in our animals model for biocompatibility in terms of red blood cell aggregation.

3: Measured microvascular apparent blood viscosity and shear stress at the endothelial vessel wall, and systemic blood apparent viscosity.

4: Determined apoptosis-necrosis outcomes as a function of time (1 hour, 2–3 hours, one day) during reduced Htc with a low and high viscosity plasma expander perfusion as in 1.

Basic questions surrounding blood viscosity in vivo show that understanding of its functional role is incomplete. It has been assumed that lowering blood viscosity is beneficial. This assertion may be true when blood viscosity is pathologically high. However, several decades of hemodilution studies, aimed at increasing blood fluidity had not really tested the benefit of lowered blood viscosity, but rather had demonstrated the capacity of the organism to compensate for reduced oxygen carrying capacity with systemic hemodynamic adjustments. The transfusion trigger for humans, i.e., where the reduction of red blood cell mass is deemed to imperil tissue oxygenation, is set at about 7 g Hb/dl or a 50% loss of red blood cells, which is close to the limit of the organism's capacity to adjust for oxygen delivery capacity. Our new interpretation is that it is also be the limit for the compensation of reduced blood viscosity. Blood transfusions called for once the trigger is reached may be necessary to correct for both the reduced oxygen carrying capacity and reduced viscosity in the absence of the present invention. Under the assumption that reduced blood viscosity is not harmful and may be beneficial, patients have been massively exchanged with Ringer's lactate. Even when this exchange is limited to the reduction of blood hemoglobin to 7 g/dl, a massive volume exchange with Ringer's lactate significantly reduces plasma protein and plasma viscosity. The effects of this perturbation in terms of FCD is not known and there is evidence that endothelial cell necrosis/apoptosis is significantly increased due to the resulting low shear stress condition.

Method of Approach

The systemic hemodynamic effects of lowering blood viscosity to about half of its normal value, through the reduction of hematocrit is well understood, although the specific effect of this maneuver on capillary pressure has not been measured. We did this and characterized the microvascular hemodynamics in the microcirculation, of the limiting condition for oxygen carrying capacity/blood viscosity reduction that provides a safe margin of tissue perfusion. We define this margin of safety as characterized by normal functional capillary density and 50% tissue oxygenation relative to normal. We define the microcirculation to extend from arteriolar vessels of 120 $\mu$m diameter to similar size venules. Approximately 75% of vascular resistance is comprised by these vessels. We assume that up to the presently used transfusion trigger (approximately set at 50% of normal hematocrit, 7 g Hb/dl) microvascular function is preserved. This principle guides our design, so that the physical properties of the fluid to be used to maintain/restitute volume beyond the transfusion trigger cause the blood/plasma expander mixture to achieve the viscosity present at the transfusion trigger.

REFERENCES

Intaglietta, M. and B. W. Zweifach. Microcirculatory basis of fluid exchange". In: *Advances in Biological and Medical Physics.* 15:111–159, 1973.

Kanzow, G., Pries, A. R., and P. Gaehtgens. Analysis of the hematocrit distribution in the mesenteric microcirculation, *Int. J. Microcirc. Clin. Exp.* 1:67–80, 1982.

Klitzman, B. and P. C. Johnson. Capillary network geometry and red cell distribution in hamster cremaster muscle. *Am. J. Physiol.* 242:H211–H219, 1982.

Lipowsky, H. H., Usami, S., and S. Chien. In vivo measurements of hematocrit and apparent viscosity in the microvasculature of cat mesentery. *Microvasc. Res.,* 19:297–319, 1980.

Lipowsky, H. H. Mechanics of blood flow in the microcirculation. In: Handbook of Bioengineering, (R. Skalak, S. Chien, eds.). McGraw-Hill Book Co., New York, ch. 18, 1987.

Sarelius, I. H. and B. R. Duling. Direct measurement of microvessel hematocrit, red cell flux, velocity and transit time. *Am. J. Physiol.* 243:HIOI8–HIO26, 1982.

Schmid-Schönbein, G. W. and B. W. Zweifach. RBC velocity profiles in arterioles and venules of the rabbit. *Microvasc. Res.* 10:165–179, 1975.

BACKGROUND

Formulation and Administration

The materials and solutions of the present invention can be prepared by methods well-known in the field of blood substitutes and plasma expanders. Those techniques can be readily utilized by one skilled in the art and so will not be repeated here.

In general, components should be of pharmaceutical grade (at least for human use), and should be sterile or be sterilized before use. Sterilization may be by any method or combination of methods accepted in the field which is compatible with the particular composition and expected use. Examples include heat sterilization, and filter sterilization.

It is highly preferable that a composition is approved for use with a particular mammal or mammals, especially for use in humans, but also preferred for veterinary use. The approval would be by the accepted regulatory body, e.g., the U.S. Food, and Drug Administration or the equivalent European or Japanese bodies.

The administration of these materials of the present invention will be somewhat variable, depending on the molecule, formulation and clinical condition being treated. However, there are some general principles that can be applied, and those skilled in the art will readily recognize the appropriate specifics or readily be able to select appropriate administration conditions.

Additionally, the molecules used for increasing viscosity will generally be capable of significant water absorption, acting to raise the intravascular volume up to several times their infusion volume (e.g., 2× or 3×) if administered rapidly. Therefore, depending on the desired indication, the infusion rate may range from rapid infusion (e.g., to restore blood volume in acute shock states) to slow infusion (e.g., where their desired effect is to slowly raise or prevent the fall in plasma viscosity).

Their use can be titrated by measurement of the plasma/blood viscosity in non-acute conditions where they are used to maintain capillary flow over days rather than hours. Normal human serum viscosity ranges from about 1.4 to 1.8 cp; in most cases it is desirable to increase plasma viscosity to at least this range. Generally, blood viscosity for human application will be no more than 5 cp.

For acute hemodilution (e.g., Hb<7 g/dL for humans) or burns, the range of volume infusion is likely to be from little as 100 ml up to 1,000 ml given intravenously over 30 minutes to 4 hours, e.g., over 30 minutes, 45 minutes, 1 hr, 1½ hrs, 2 hrs, 2½ hrs, 3 hrs, 3½ hrs, 4 hrs, or over a time in a range between any two of the listed times. In appropriate circumstances it may also be desirable to use longer times, e.g., 6, 10, 14, or 18 hrs. Thus, in preferred embodiments, for humans the infusion volume of the viscosity-increasing solution may be in the range of 100–300 ml, 200–500 ml, 400–700 ml, 500–800 ml, or 700–1000 ml.

For more chronic use, in preferred embodiments, the range-of volume infusion will be from as little as 100 ml over 24 hours up to 500 ml over 24 hours, e.g., in the range 100–200 ml, 200–300 ml, 300400 ml, or 400–500 ml. Other infusion times can also be used.

Exemplary formulations and volumes of solutions of this invention for administration to humans are as follows:

For use where blood loss of 2.5 liters or greater has occurred which has been treated with Ringer's lactate, saline, or other conventional plasma expander, 0.5 liters of a 20 cp solution can be used. The volume would be varied depending on the size of the patient and the level of hemodilution that has occurred. For example, the volume may instead be 300 ml, 400 ml, 600 ml or other appropriate volume to obtain the desired viscosity increase.

For use where large volume blood loss has occurred, but where the loss has not been treated with conventional plasma expanders, a 7, 8, 9, or 10 cp solution can be used in a volume as indicated for the preceding case.

Clearly, other formulations could readily be used in volumes adapted to the particular application.

Clinical measurement of plasma viscosity is currently not routinely done in clinical medicine. Beneficially, a simple, portable medical device to make such determinations would be provided in the pre-hospital, trauma, critical care, and operative settings.

EXAMPLES

Introduction

The effects of increasing blood viscosity during extreme hemodilution on capillary perfusion and tissue oxygenation was investigated in the awake hamster skinfold model. Two isovolemic hemodilution steps were performed with 6% Dextran 70 [molecular weight (MW)=70,000] until systemic hematocrit (Hct) was reduced by 65%. A third step reduced Hct by 75% and was performed with the same solution [low viscosity (IV)] or a high-molecular-weight 6% Dextran 500 solution [MW=500,000, high viscosity (HV)]. Final plasma viscosities were 1.4 and 2.2 cP (baseline of 1.2 cP). Hct was reduced to 11.2±1.1% from 46.2±1.5% for LV and to 11.9±0.7% from 47.3±2.1% for HV. HV produced a greater mean arterial blood pressure than LV. Functional capillary density (FCD) was substantially higher after HV (85±12%) vs. LV (38±30%) vs. baseline (100%). $Po_2$ levels measured with Pd-porphyrin phosphorescence microscopy were not statistically changed from baseline until after the third hemodilution step. Wall shear rate (WSR) decreased in arterioles and venules after LV and only in arterioles after HV. Wall shear stress (WSR×plasma viscosity) was substantially higher after HV vs. LV. Increased mean arterial pressure and shear stress-dependent release of endothelium-derived relaxing factor are possible mechanisms that improved arteriolar and venular blood flow and FCD after HV vs. LV exchange protocols.

Hemodilution changes the physical properties of blood by reducing the number of circulating red blood cells (RBCs), thus decreasing the oxygen-carrying capacity of blood and blood viscosity. During moderate levels of hemodilution, reduction of the systemic hematocrit (Hct) up to 50% is compensated for with a decrease in blood viscosity leading to an increased blood flow velocity and decreased diffusional oxygen exit from arterioles, resulting in augmented or maintained oxygen delivery to tissue (Messmer, et al., *Adv. Microcirc.* 4: 1–77, 1972; Mirhashemi, et al., *Int. J. Microcirc. Clin. Exp.* 6: 359–369, 1987). In addition, reduction of systemic Hct during intentional hemodilution is not mirrored at the microcirculatory level, since capillary Hct is sustained near control levels (Lipowsky and Firrell, *Am. J. Physiol.* 250: H908–H922, 1986; Mirhashemi, et al., *Am. J. Physiol.* 254: H411–H416, 1988; Tigno and Henrich, *Acta. Med. Phil.* 22: 5–12, 1986; Tigno and Henrich, *Acta. Med. Phil.* 22: 53–58, 1986), thus maintaining tissue oxygenation.

When systemic Hct is reduced by 60% or more (Hct that is 40% of normal or less) there is a significant decrease in blood viscosity and a lowering of blood hemoglobin concentration to levels where oxygen carrying capacity is marginal and tissue oxygenation may be impaired. Under these conditions, oxygen delivery to tissue hinges on increasing oxygen extraction and maintaining the surface area for exchange, which is determined by the functional capillary density (FCD).

Blood viscosity is mainly determined by the concentration of RBCs, whereas the shear rate at the wall is a function of the plasma viscosity (Gustafsson, et al., *Am. J. Physiol.* 241: H513–H518, 1981). The viscous properties of the plasma and the plasma layer in setting vessel wall shear stress are particularly significant in the microcirculation due to the migration of RBCs to the centerline of the vessel (Barbee and Cokelet, *Microvasc. Res.* 3: 6–16, 1971). Viscosity and flow velocity of blood define shear stress at the blood vessel wall, which stimulates vascular endothelium to produce vasoactive substances such as prostacylin (Frangos, et al., *Science* 227: 1477–1479, 1985) and nitric oxide [NO (Buga, et al., *Hypertension* 17: 187–193, 1991)]. In moderate hemodilution, the reduction in viscosity is compensated by the increased flow; thus the shear stress sensed by the endothelium does not change significantly.

During extreme hemodilution, the cardiac output can no longer be sustained, and consequently blood flow will not develop the sufficient shear stress required for shear stress-dependent release of mediators, resulting in a reduced capillary perfusion. This is not the situation found in moderate hemodilution where the reduction in Hct and thus blood viscosity is compensated for by an increased blood velocity. The shear stress sensed by the endothelium in this situation is actually increased due to the increased flow and an essentially unchanged plasma viscosity. To determine if viscosity is a factor involved in regulating FCD and microvascular flow during extreme hemodilution, we designed a study in which we lower oxygen carrying capacity but augment plasma viscosity by exchanging blood with a high-viscosity (HV) ultrahigh-molecular weight dextran solution. Increased plasma viscosity at extreme hemodilution levels was analyzed in terms of microvascular tone, blood flow, FCD, and oxygen distribution to determine the functional state of the microvasculature under these conditions.

Example 1

Materials and Methods

Animal Preparation

Investigations were performed on 55- to 65-g golden Syrian hamsters (Simonsen, Gilroy, Calif.). Animal handling and care were provided following the procedures outlined in the *Guide for the Care and Use of Laboratory Animals* (National Research Council, 1996). The study was approved by the local Animal Subjects Committee. The hamster chamber window model is widely used for microvascular studies in the unanesthetized state, and the complete surgical technique is described in detail elsewhere (Colantuoni, et al., *Am. J. Physiol.* 246: H508–H517, 1984; Endrich, et al., *Res. Exp. Med.* (*Berl*) 177: 135–143, 1980). Briefly, the animal was prepared for chamber implantation with a 5 mg/kg ip injection of pentobarbital sodium anesthesia. After hair removal, sutures were used to lift the dorsal skin away from the animal, and one frame of the chamber was positioned on the animal's back. A chamber consisted of two identical titanium frames with a 15-mm circular window. With the aid of backlighting and a stereomicroscope, one side of the skinfold was removed following the outline of the window until only a thin monolayer of retractor muscle and the intact subcutaneous skin of the opposing side remained. Saline and then a cover glass were placed on the exposed skin held in place by the other frame of the chamber. The intact skin of the other side was exposed to the ambient environment. The animal was allowed at least 2 days for recovery; then its chamber was assessed under the microscope (×650) for any signs of edema, bleeding, or unusual neovascularization.

Barring these complications, the animal was anesthetized again with pentobarbital sodium. Arterial and venous catheters were implanted in the carotid artery (PE-50) and jugular vein (PE-10), respectively. The catheters were filled with a heparinized saline solution (30 IU/ml) to ensure their patency at the time of experiment. Catheters were tunneled under the skin and exteriorized at the dorsal side of the neck where they were attached to the chamber frame with tape. The experiment was performed after at least 24 h but within 48 h after catheter implantation.

Inclusion criteria. Animals were suitable for the experiments if 1) systemic parameters were within normal range, namely, heart rate (HR)>320 beats/min, mean arterial blood pressure (MAP)>80 mmHg, systemic Hct>45%, and arterial $Po_2$>50 mmHg; and 2) microscopic examination of the tissue observed under ×650 magnification did not reveal signs of edema or bleeding.

Systemic Parameters

MAP was measured continuously over the entire experimental period, except during the actual blood exchange, by attaching the arterial catheter to a pressure transducer (Beckman Recorder; Spectramed Pressure Transducer). HR was determined from the pressure trace. Hct was measured from centrifuged arterial blood samples taken in heparinized capillary tubes (Readacrit Centrifuge; Clay Adams, Division of Becton-Dickinson, Parsippany, N.J.).

Blood Chemistry and Rheology

Arterial blood sampled in two heparinized capillary tubes from the carotid artery catheter was immediately analyzed for arterial $Po_2$ $Pco_2$, and pH at 37° C. using a pH/blood gas analyzer (model 248; Chiron Diagnostics, Norwood, Mass.). Hemoglobin content of blood was determined from a drop of blood using a handheld photometric device (B-Hemoglobin Photometer Hemocue). Blood samples for viscosity and colloid osmotic pressure measurements were quickly withdrawn from the animal with a heparinized 3-ml syringe at the end of the experiment for immediate analysis or refrigerated for next-day analysis. The small animal size allowed for only ~2 ml of blood to be withdrawn from the animal after an experiment, which was not sufficient volume to measure colloid osmotic pressure, blood viscosity, and plasma viscosity. Because of the small sample volume, only one or two of these parameters could be measured in each animal. Measurements were then combined and taken to be representative of the entire group. Blood samples were centrifuged, and colloid osmotic pressure in the plasma was measured using a colloid osmometer (model 420; Wescor, Logan, Utah). Calibration of the osmometer was made with a 5% albumin solution using a 30,000 molecular weight cut-off membrane (Amicon, Danvers, Mass.). The viscosity of plasma and whole blood was determined at a shear rate of $160\,s^{-1}$ at 37° C. in a 500-$\mu$m-diameter capillary viscometer (Reinhart, et al., *Euro. J. Clin. Pharm.* 104: 921–931, 1984).

Microhemodynamic Parameters

Detailed mappings were made of the chamber vasculature so that the same vessels studied in control could be followed throughout the experiment. Functional capillaries, defined as those capillary segments that have RBC transit of at least a single RBC in a 30-s period, were assessed in 10 successive microscopic fields, totaling a region of ~0.46 $mm^2$. Observation of the fields was done systematically by displacing the microscopic field of view by a field width in 10 successive steps in the lateral direction (relative to the observer). Each step was viewed on the video monitor and was 240 $\mu$m long when referred to the tissue. The first field was chosen by a distinctive anatomic landmark (i.e., large vascular bifurcation) to easily and quickly reestablish the same fields and vessels at each observation time point. Each field had between two and five capillary segments with RBC flow. FCD ($cm^{-1}$), i.e., total length of RBC perfused capillaries divided by the area of the microscopic field of view, was evaluated by measuring and adding the length of capillaries that had RBC transit in the field of view. The relative change in FCD from baseline levels after each intervention is indicative of the extent of capillary perfusion.

Arteriolar and venular blood flow velocity were measured on-line using the photodiodelcross-correlator system of Intaglietta et al. (Intaglietta, et al., *Microvasc. Res.* 10: 165–179, 1975; Fiber Optic Photo Diode Pickup and Velocity Tracker model 102B; Vista Electronics, San Diego, Calif.). The measured centerline velocity was corrected according to vessel size to obtain the mean RBC velocity (V; see Lipowsky and Zweifach, *Microvasc. Res.* 15: 93–101, 1978). The video image shearing technique was used to measure vessel diameter (D) on-line (Digital Video Image Shearing Monitor model 908; Vista Electronics). Blood flow rate ($\dot{Q}$) is equal to the mean RBC velocity times the cross-sectional area of the vessel and was calculated according to the expression $\dot{Q}=V\cdot\pi(D/2)^2$. Wall shear stress (WSS) is defined by the formula $$WSS=WSR\cdot\eta$$

where WSR is the wall shear rate expressed as 8·VD, and $\eta$ is the plasma viscosity.

Intravascular and Extravascular $Po_2$ Measurements

Oxygen tension measurements were made using palladium-porphyrin phosphorescence quenching microscopy (Torres Filho and Intaglietta, *Am. J. Physiol.* 34: H1434–H1438, 1993; Wilson, *Adv. Exp. Med. Biol.* 333: 225–232, 1993), which is based on the relationship between the decay rate of excited palladium-mesotetra-(4-carboxyphenyl)porphyrin (Porphyrin Products, Logan, Utah) bound to albumin and the partial pressure of oxygen according to the Stem-Volmer equation (Wilson, *Adv. Exp. Med. Biol.* 333: 225–232, 1993). Animals received a slow intravenous injection of 15 mg/kg body wt at a concentration of 10.1 mg/ml of the phosphorescence dye ~10 min before $Po_2$ measurements. Albumin exchange between plasma and tissue allows sufficient concentrations of albumin-bound dye within the interstitium to achieve an adequate signal-to-noise ratio for interstitial $Po_2$ measurements (Vanderkooi, et al., *J. Biol. Chem.* 252: 5476–5482, 1987). Simultaneous tissue $Po_2$ measurements using this system and the classic microelectrode technique have found nearly identical values (Buerk, et al., *Microcirculation* (accepted for publication)).

In our system described in detail elsewhere (Torres Filho and Intaglietta, *Am. J. Physiol.* 34: H1434–H1438, 1993), intravascular measurements are made by placing an optical rectangular window within the vessel of interest, and the longest side of the rectangle is positioned parallel to the vessel wall. Intravascular $Po_2$ measurements were made in large feeding arterioles, smaller arcading arterioles, large venules, and smaller collecting venules. Tissue $Po_2$ measurements were made in interstitial regions devoid of large vessels with a 10 $\mu$m by 10 $\mu$m optical window to obtain an estimate of the lowest oxygen level within the chamber (Kerger, et al., *Am. J. Physiol.* 270: H827–H836, 1.996). The decay curves are analyzed off-line, using a standard single exponential least squares numerical fitting technique. Resultant time constants are applied to the Stern-Volmer equation to calculate $Po_2$, where the quenching constant and the phosphorescence lifetime in the absence of oxygen measured are 325 $mmHg^{-1}\cdot s^{-1}$ and 600 $\mu$s, respectively, in this system. The phosphorescence decay due to quenching at a specific $Po_2$ yields a single decay constant (Vanderkooi, et al., *J. Biol. Chem.* 252: 5476–5482, 1987), and in vitro calibration has been demonstrated to be valid for in vivo measurements.

Acute Isovolemic Hemodilution

Progressive hemodilution to a final systemic Hct level of 25% of baseline was accomplished with three isovolemic exchange steps. The volume of each exchange was a percentage of the animal's total blood volume, estimated at 7% of the body weight. The level 1 exchange of 40% of the blood volume was followed by level 2 and 3 exchanges, where 35% of the blood volume was exchanged at each step. Level 1 exchange results in a moderate hemodilution. Level 2 and 3 exchanges result in an extreme hemodilution where systemic Hct falls below 40% of normal. Using an infusion pump, we first passed the exchange solution through an in-line 0.22-$\mu$m syringe filter and then into the animal via the jugular vein catheter at a rate of 100 $\mu$l/min. Blood was simultaneously withdrawn by hand from the carotid artery at the same rate, a method found to be more accurate than using the automated syringe pump where the detection of catheter obstruction usually due to blood clotting is delayed. Because of the size of the animals, a slow rate of exchange was chosen to ensure a stable blood pressure during the exchange period. The animal was given a 5-min recovery period before data acquisition.

Experimental Design

The unanesthetized animal was placed in a restraining tube where it had access to wet feed during the entire experimental period. The animal was given 30 min to adjust to the tube environment before the control systemic parameters (MAP, HR, blood gases, and Hct) were measured. The conscious animal in the tube was then affixed to the microscopic stage of a transillumination intravital microscope (Leitz Ortholux H). The tissue image was projected onto a charge-coupled device camera (COHU 4815-2000) connected to a videocassette recorder (AG-7355; Panasonic) and viewed on a monitor (PVM-1271Q; Sony). The baseline FCD was assessed using a ×25 (numerical aperture=0.7, Leitz) salt water objective. For easier detection of RBC passage, the contrast between RBCs and tissue was enhanced with a BG12 (420 nm) bandpass filter. The animal, still situated in the restraining tube, was then repositioned on an inverted microscope (IMT-2 Olympus, New Hyde Park, N.Y.) equipped with a ×20 dry objective (numerical aperture=0.46; Olympus), where arterioles and venules chosen for study (4–7 of each type) were characterized by their blood flow velocity and caliber. Microscopic images were televised on another identical video system. The animal was repositioned on each microscope after each exchange to follow the changes of the microvascular parameters. Fields of observations and vessels were chosen for study at locations in the tissue where the vessels were in sharp focus. The same fields and vessels were investigated throughout the experiment so that comparisons are related directly to baseline levels.

Animals were randomly divided into the following five experimental groups: 1) control (no hemodilution); 2) level 1 [hemodilution with Dextran 70 (6% wt/vol mean molecular weight of 70,000; Pharmacia) to Hct of 60% of baseline]; 3) level 2 (hemodilution with Dextran 70 to Hct of 40% of baseline); 4) level 3 low viscosity (LV, hemodilution with Dextran 70 to Hct of 25% of baseline); 5) level 3 HV [hemodilution with Dextran 70 to Hct of 35% of baseline followed by hemodilution with 6% wt/vol Dextran 500 (mean molecular weight: 500,000; Pharmacia) in 0.9% normal saline to Hct of 25% of baseline].

Immediately after baseline systemic measurements, animals in the control group received a bolus injection of palladium-porphyrin dye, and measurements of oxygen distribution and microvascular hemodynamics were performed. In the experimental exchange groups, successive hemodilution was performed after baseline systemic, microvascular, and hemodynamic characterization. After each exchange and the ensuing stabilization period, measurements were performed following the schedule shown in FIG. 1, where exchanges begin every hour, i.e., the second exchange commences exactly 1 h after the first exchange. Repeated $Po_2$ measurements over time were not made to reduce possible complications from light and dye overexposure, which may affect the microhemodynamic response of the tissue. Blood samples were withdrawn from level 3 exchange animals at the end of the experiment for subsequent analysis of viscosity and colloid osmotic pressure. The duration of the experiments was between 1 and 5 h depending on the degree of hemodilution.

The concentration of the high-molecular-weight Dextran 500 solution and the exchange protocol were determined from pilot studies where the animals were hemodiluted to the exchange level 3 with a 25% wt/vol solution, and their venular microvasculature was observed for signs of RBC aggregation, since theological disturbances appear in vessels with low shear (Gustafsson, et al., *Am. J. Physiol.* 241: H513–H518, 1981). Pilot studies found that animals could withstand an entire third exchange with 6% Dextran 500 solution without visible in vivo RBC aggregation. To avoid this critical concentration of Dextran 500, the level 3 exchange protocol began with 10% of the total blood volume exchange using 6%. Dextran 70 solution followed by 25% of the total blood volume exchange with the 6% Dextran 500. This procedure ensured an increased blood viscosity compared with a level 3 exchange made solely with Dextran 70 and an absence of rheological complications. Pertinent physical properties of the exchange solutions used in this study are listed in Table 1.

TABLE 1

Intrinsic physical characteristics of the dextran solutions

| | Average Molecular Mass, Da | Viscosity,* cP | COP, mmHg |
|---|---|---|---|
| Dextran 70 (6%) | 70,000 | 2.8 | 49.9 |
| Dextran 500 (6%) | 500,000 | 6.4 | 31.6 |

*Shear rate of 160 $a^{-1}$ at 37° C.;
COP, colloid osmotic pressure.

Data Analysis

Results are presented as means±SD unless otherwise noted. Data are presented relative to levels at baseline. All measurements were compared with their levels at baseline before the blood exchange except for the $Po_2$ measurements in which oxygen levels were compared between groups of animals. For repeated measurements, time-related changes were assessed by analysis of variance. Comparison between different groups of animals was performed with the Student's t-test and the Mann-Whitney rank sum test. Multiple comparisons were made with the Student-Newman-Keuls test (SigmaStat Windows 95/v2.0; Jandel Scientific). Changes were considered statistically significant at P<0.05.

Example 2

Results of Hamster Sminfold Experiments

Thirty-nine animals were entered into this study and assigned randomly to the following protocol exchange groups: control (n=9); level 1 (n=7); level 2 (n=6); level 3 LV (n=9); level 3 HV (n=8). All animals tolerated the entire hemodilution protocol without visible signs of discomfort except two out of nine animals in the level 3 LV exchange group who experienced a decline of MAP below 50 mmHg and a complete shutdown in flow to the subcutaneous vascular bed under study.

Systemic and Blood Gas Parameters

Changes in the systemic and blood gas parameters for each experimental group are presented in Table 2. There were no statistically significant differences between experimental groups before the exchange protocol. Systemic Hct after level 1 and 2 exchange was 0.56±0.04 and 0.40±0.04 of baseline (P<0.05 relative to baseline), respectively. Level 3 LV and HV exchange reduced the systemic Hct to 0.24±0.02 and 0.25±0.02 of baseline, respectively, which were statistically reduced from baseline (P<0.05) but not statistically different from each other.

MAP was not changed from baseline in the level 1 exchange group, but upon further hemodilution with Dextran 70 MAP fell to 0.92±0.05 and 0.62±0.10 of baseline in level 2 and level 3 LV groups, respectively (P<0.05). In the level 3 HV group, MAP fell to 0.90±0.09 of baseline (P<0.05), a statistically higher level than the MAP after level 3 LV exchange. HR was not affected by any of the hemodilution protocols.

Systemic arterial blood gas analysis showed a statistically significant rise in $Po_2$ from baseline and a fall in $Pco_2$ with increasing degree of hemodilution in all groups. There were no statistical differences in arterial blood gases between the level 3 exchange groups. Blood pH was not statistically changed from baseline among all the experimental groups.

TABLE 3

Rheological properties and colloid osmotic pressure

| | Blood Viscosity, cP | n | Plasma Viscosity, cP | n | COP, mmHg | n |
|---|---|---|---|---|---|---|
| Level 3 LV | 2.12 ± 0.35*† | 3 | 1.38 ± 0.14*† | 3 | 16.7 ± 1.3 | 3 |
| Level 3 HV | 2.80 ± 0.22*† | 5 | 2.19 ± 0.08*† | 3 | 15.6 ± 0.9 | 5 |
| Whole blood | 4.47 ± 0.50 | 8 | 1.20 ± 0.04 | 4 | 17.5 ± 1.7 | 6 |

Values are means ± SD;
n, no. of animals studied.
*P < 0.05 vs. whole blood;
†P < 0.05 between groups, low and high viscosity.

Microhemodynamics

Vascular tone. The changes in the diameter of large feeding and small arcading arterioles (range, 23–95 μm) and small collecting venules and large venular vessels (range, 24–203 μm) were measured after each hemodilution step. FIG. 2A shows that arteriolar diameter was unchanged after level 1 exchange. Upon further blood exchange to level 2, arterioles dilated to 1.15±0.28 (n=46, P<0.001) of baseline. This trend reversed after level 3 LV exchange, resulting in a slight arteriolar vasoconstriction to 0.94±0.15 (n=49, P<0.05) of baseline. After the level 3 HV exchange, arteriolar diameter remained dilated at 1.22±0.28 (n=47, P<0.001) of baseline.

Venular changes due to the hemodilution protocol are shown in FIG. 2B as a function of the Hct. Venules responded to level 1 exchange by constricting to 0.95±0.13 of baseline (n=42, P<0.05) and then returning to baseline levels after level 2 exchange (n=36). When the exchange

TABLE 2

Macrohemodynamic parameters before and after blood exchange

| | Level 1 | | Level 2 | | Level 3 LV | | Level 3 HV | |
|---|---|---|---|---|---|---|---|---|
| | Before | After exchange | Before | After exchange | Before | After exchange | Before | After exchange |
| Hct, % | 49.5 ± 1.4 | 0.56 ± 0.04* | 48.8 ± 1.2 | 0.40 ± 0.04* | 46.2 ± 1.5 | 0.24 ± 0.02* | 47.8 ± 2.0 | 0.25 ± 0.02* |
| MAP, mmHg | 100.9 ± 5.6 | 0.99 ± 0.05 | 97.5 ± 5.5 | 0.88 ± 0.08* | 92.7 ± 9.6 | 0.62 ± 0.10*† | 96.9 ± 9.1 | 0.90 ± 0.09*† |
| HR, beta/min | 434.3 ± 51.3 | 0.97 ± 0.07 | 393.3 ± 18.9 | 1.04 ± 0.06 | 410.0 ± 46.6 | 0.95 ± 0.15 | 422.6 ± 26.1 | 1.01 ± 0.07 |
| [Hb], g/dl | 14.4 ± 0.6 | 0.61 ± 0.38* | 14.2 ± 0.9 | 0.89 ± 0.28* | 13.9 ± 1.1 | 0.25 ± 0.02* | 14.3 ± 0.9 | 0.27 ± 0.02* |
| $Pao_2$, mmHg | 60.2 ± 7.7 | 1.19 ± 0.15* | 65.9 ± 5.1 | 1.25 ± 0.11* | 59.7 ± 7.3 | 1.76 ± 0.16* | 56.1 ± 3.5 | 1.82 ± 0.12* |
| $Paco_2$, mmHg | 55.4 ± 3.7 | 1.03 ± 0.06 | 57.3 ± 3.7 | 0.62 ± 0.14* | 62.1 ± 7.5 | 0.76 ± 0.18* | 65.8 ± 4.6 | 0.72 ± 0.08* |
| Arterial pH | 7.33 ± 0.2 | 1.00 ± 0.00 | 7.35 ± 0.03 | 1.00 ± 0.01 | 7.36 ± 0.04 | 0.99 ± 0.01 | 7.36 ± 0.03 | 1.00 ± 0.01 |

Values are means ± SD. Before values are absolute values obtained at baseline conditions. After exchange values are presented as a fraction of the Before values and serve as an indicator of the relative change from baseline. No significant differences were detected between the baseline values of each group or between the values after the second exchange before the exchange with the high-viscosity solution Dextran 500, Level 1, hemodilution with Dextran 70 (5% wt/vol mean mol wt of 70,000); level 2, hemodilution with Dextran 70 to hematocrit of 40% of baseline; level 3 low viscosity (LV), hemodilution with Dextran 70 to hematocrit of 25% of baseline; level 3 high viscosity (HV), hemodilation with Dextran 70 to hematocrit of 35% of baseline followed by hemodilution with 6% wt/vol Dextran 600 (mean mol wt 500,000) in 0.9% normal saline to hematocrit of 25% of baseline; Hct, systemic hematocrit; MAP, mean arterial blood pressure; HR, heart rate; [Hb], hemoglobin content of blood; $Pao_2$, arterial partial $O_2$ pressure; $Paco_2$, arterial partial pressure of $CO_2$,
*P < 0.05 vs. baseline;
†P < 0.05, level 3 LV vs. level 3 HV.

Physical Properties of Blood

Comparison of rheological properties and colloid osmotic pressure of the blood after level 3 LV and HV exchange is presented in Table 3. Changes in blood and plasma viscosity were statistically different from baseline and between HV and LV groups (P<0.05). Blood viscosity was reduced to 0.47 and 0.63 of baseline, and plasma viscosity was increased to 1.15 and 1.83 of baseline levels for level 3 exchange LV and HV groups, respectively. Colloid osmotic pressure was statistically unchanged during the progressive hemodilution.

protocol was continued to the level 3 LV protocol, the venules constricted to 0.85±0.20 (n=37, P<0.001) of baseline. Level 3 HV protocol did not change venular diameters from baseline levels (n=38).

RBC velocity and blood flow. FIG. 3 shows the change in RBC velocity in arterioles (A) and venules (B) as a function of the Hct. An increase in both arteriolar and venular RBC velocity was detected after level 1 exchange to 1.67±1.03 (P<0.05) and 1.55±1.23 (P<0.05) of baseline, respectively. After level 2 exchange, arteriolar RBC velocity remained increased from baseline (1.39±0.93, P<0.05), whereas venular RBC velocity returned to baseline levels. Level 3 LV exchange reduced both arteriolar and venular RBC velocity to 0.67±0.58 and 0.70±0.76 of baseline, respectively (P<0.05). Level 3 HV exchange did not alter RBC velocity from baseline levels in either vessel type.

The relationships between arteriolar and venular blood flow after the hemodilution protocols and Hct are presented in FIG. 4. The results are given as means±SE to show the trend of this parameter calculated from vessel diameter and RBC velocity. Both arteriolar and venular blood flow were statistically increased from baseline after level 1 and level 2 exchange. Upon further hemodilution with Dextran 70 these increased levels could not be sustained, and blood flow was statistically reduced from baseline levels in both arterioles and venules. However, level 3 HV exchange caused a return of the arteriolar and venular blood flow to baseline levels.

Wall Shear Rate

Wall shear rate ($s^{-1}$) is calculated using the diameter and mean velocity of each vessel studied after level 3 IV and HV exchanges. The calculated values of wall shear rate are presented as means±SE to show the trend rather than the distribution of the parameter. Before the exchange protocol, there were no statistically significant differences in wall shear rate ($s^{-1}$) among the arterioles (LV: 614.5±35.0; HV: 574.5±34.4) and venules (LV: 107.6±18.0; HV: 146.7±17.9) in each group. After the level 3 LV exchange, arteriolar and venular wall shear rate ($s^{-1}$) were reduced to 0.68±0.09 (P<0.001) and 0.65±0.15 (P<0.001) of baseline. Level 3 HV exchange decreased arteriolar wall shear rate to 0.82±0.10 (P<0.01) of baseline. In the venules, wall shear rate was 1.36±0.21 of baseline and not statistically different from baseline. Statistical comparison between the LV and HV groups after the exchange protocol found no statistical difference in arteriolar wall shear rate. However, level 3 HV exchange did significantly increase wall shear rate relative to the LV exchange protocol in venules (P<0.001).

Functional Capillary Density

FIG. 5 shows the effect of hemodilution on the length of RBC perfused capillaries per unit area. FCD after level 1 exchange was 0.93±0.05 of baseline and not statistically different from baseline. Level 2 exchange reduced FCD to 0.84±0.04 of baseline (P<0.05). FCD was further reduced after level 3 LV and HV to 0.38±0.38 and 0.85±0.12 of baseline, respectively (P<0.05). A greater increase in capillary perfusion was obtained after level 3 exchange with the HV than with the LV protocol (P<0.05). This preparation under normal conditions and during the course of the experimental procedures shows a decrease of FCD of 13% over a period of 6 h. Therefore, the loss in FCD found after level 2 and level 3 HV is near the expected change of this parameter.

Microvascular Oxygen Distribution

Oxygen distribution was measured in the animals that had blood flow to the tissue under study. The effect of the hemodilution with Dextran 70 (level 1, 2, and 3 LV) and with augmented plasma viscosity using high molecular-weight Dextran 500 (level 3 HV) for arterioles, venules, and tissue is presented in the histograms of FIG. 6. The median and quartiles of each distribution are listed in Table 4. Level 1 and 2 exchange groups did not show statistical changes in arteriolar, venular, and tissue $Po_2$ histograms from the control group. However, the shape of the three distributions narrowed relative to the control group after level 1 exchange, and the greater separation between the mean arteriolar and venular $Po_2$ suggests an increased oxygen extraction. After level 2 exchange, there is a shift in the arteriolar $Po_2$ toward higher values; however, the changes were not statistically different from the control group. Level 3 exchange with both LV and HV fluids caused a widening of the arteriolar $Po_2$ histogram as evidenced by the 25 and 75% quartiles, resulting in a decreased median $Po_2$. Both venular and tissue histograms for level 3 exchange were shifted completely to the left. The $Po_2$ histograms obtained after level 3 LV and HV exchange were significantly different from control but were statistically unchanged from each other.

Example 3

Discussion of Hamster Experimental Results

A major finding is that normal levels of tissue perfusion in terms of arteriolar and venular blood flow and the FCD could be obtained during extreme hemodilution when plasma viscosity is increased by the addition of a high-molecular-weight Dextran 500 solution in the blood volume replacement fluid, a scenario that could not be achieved with a lower-viscosity solution. These results suggest that an increase in plasma viscosity, thus returning whole blood viscosity toward baseline conditions, elicits a regulatory mechanism that becomes inactivated during extreme hemodilution with a lower-viscosity fluid.

TABLE 4

| | Microvascular oxygen tension distribution | | | | | | | | |
|---|---|---|---|---|---|---|---|---|---|
| | Control | n | Level 1 | n | Level 2 | n | Level 3 LV | n | Level 3 HV | n |
| Arteriolar | 51.8 (45.0, 58.8) | 58 | 55.2 (51.2, 59.7) | 44 | 57.8 (46.3, 62.2) | 46 | 32.9*†‡ (23.5, 48.0) | 48 | 39.0*†‡ (29.9, 49.5) | 46 |
| Venular | 32.7 (25.5, 38.8) | 56 | 29.9 (26.0, 32.2) | 42 | 29.2 (24.7, 37.9) | 36 | 0.5*†‡ (0.3, 5.1) | 32 | 1.4*†‡ (0.5, 4.4) | 34 |
| Tissue | 17.6 (12.6, 25.8) | 37 | 21.0 (17.3, 27.6) | 45 | 20.4 (15.3, 25.9) | 46 | 0.4*†‡ (0.3, 1.5) | 71 | 0.5*†‡ (0.3, 5.0) | 50 |

Data are presented as medians followed by the 25 and 75% quartiles in parentheses;
n, no. of vessels studied, Units are mmHg.
*P < 0.06 vs. control group;
†P < 0.05 vs. level 1;
‡P < 0.05 vs. level 2.

Oxygen delivery or systemic oxygen transport capacity during moderate intentional hemodilution is maintained because the decrease in the number of circulating RBCs reduces blood viscosity thereby enhancing cardiac output. Given the premise that higher blood viscosity should decrease blood flow and reduce tissue perfusion, an increase in blood viscosity, particularly with dextrans, which has been shown to cause aggregation by macromolecular bridging (Chien and Jan, *J. Supramol. Struct.* 12: 385–409, 1973), could be potentially detrimental (Gelin, *Acta Chir. Scand. Suppl.* 210: 1–130,1956; Kroemer, et al., *Euro. J. Clin. Pharm.* 31: 705–710, 1987). In our study, we found that increasing plasma viscosity was beneficial to tissue perfusion. This concept is supported by previous investigators who showed that organ blood flow and oxygen delivery were not impaired by plasma hyperviscosity. Comparison of tissue oxygenation achieved during moderate hemodilution with 3 and 6% Dextran 60, a 33% difference in plasma viscosity, showed similar elevations in $Po_2$ levels on the surface of liver and skeletal muscle (Bruckner, et al., *Infusionstherapie und Transfusionsmedizin* 20: 130–139, 1993). Investigators found that a higher-viscosity replacement fluid was able to achieve increased organ blood flow not observed with a lower-viscosity fluid. Krieter et at. (Krieter, et al., *Int J. Microcirc. Clin. Exp.* 39: 236–244, 1995) progressively hemodiluted by small infusions of a similar high-molecular-weight dextran used in the present study and found that an increase in plasma viscosity to 3 mPa·s did not compromise perfusion or oxygenation of vital organs. They proposed that the concomitant decrease in Hct from the hemodilution was completely offset by the elevated plasma viscosity, resulting in normal tissue oxygenation and organ perfusion. Use of high-molecular-weight Dextran 500 solutions (molecular weight=500,000) has also been shown to better lower mortality and limit the severity of pancreatitis (Schmidt, et al., *Am. J. Surg.* 165: 4045, 1993) over the levels achieved with lower weight dextran solutions. In further support of our finding, Waschke et al. (Waschke, et al., *Journal of Cerebral Blood Flow and Metabolism* 14: 871–876, 1994) found that cerebral perfusion was not compromised when they altered the viscosity of plasma while keeping the oxygen content of blood constant. They achieved this by performing a complete blood exchange with a fluid consisting of cell-free hemoglobin and 2% polyvinylpyrrolidone (molecular weight=400,000). Chen et al. (Chen, et al., *Am. J. Physiol.* 256: H898–H905, 1989) exchanged whole blood with a 20% wt/vol solution of Dextran 500 in blood, elevating plasma viscosity fourfold (4 mPa·s), and observed compensatory vasodilation reflected by a reduction of vascular hindrance in several vital organs, which served to maintain blood flow and nutrient transport despite the induced hyperviscosity. These investigations on the effects of induced hyperviscosity in different animals and tissues support the concept that induced plasma hyperviscosity is not detrimental to tissue perfusion and in some instances improves perfusion over lower-viscosity fluids, as shown in our study.

Our findings show that the reduction in FCD observed after level 3 LV exchange can be prevented by hemodilution using high-molecular-weight Dextran 500 to augment plasma viscosity. A mechanism directly related to an increase in plasma viscosity is the enhancement of shear stress via an increase in the viscous drag on the vessel wall. Release of vasodilators from the vascular endothelium such as NO (Buga, et al., *Hypertension* 17: 187–193, 1991) and prostacyclin (Frangos, et al., *Science* 227: 1477–1479, 1985) by endothelial cells has been shown to be shear stress induced. Increase in vessel wall shear stress by elevation of plasma viscosity using Dextran 500 has been shown to induce sustained NO-mediated dilation in the hamster cremaster muscle in vivo (de Wit, et al., *Pflug. Arch.—Eur. J. Physiol.* 434: 354–361, 1997); increasing the plasma viscosity by 64.3% led to a 24.3% dilation in large feeding arterioles. In our study, increasing the plasma viscosity by 58.7% during the last exchange with Dextran 500 led to a 28.8% arteriolar vasodilation over the levels achieved with Dextran 70 as the sole hemodilutant. Systemic vasodilation, implying a reduction in total peripheral resistance during moderate hemodilution, has also been shown to be a result of endogenous NO release (Doss, et al., *Anesthesia and Analgesia* 81: 30–34, 1995). Theoretical analysis applied to artificial blood replacement fluids suggests that lowered blood viscosity during blood substitution without proportionate increases in blood flow to maintain a constant vessel wall shear stress would lead to diminished mechanotransduction of the viscous drag by blood flow to the endothelium, resulting in vasoconstriction (Intaglietta, *Ann. Biomed. Eng.* 25: 593–603, 1997). Wall shear stress is also directly a function of fluid flow, and increases in blood flow have also been found to induce vasodilation (Smiesko and Johnson, *NIPS* 8: 34–38, 1993). In the present investigation, the increase in arteriolar and venular blood flow achieved with the HV protocol beyond that of the LV protocol suggests that the difference in wall shear stress, increase in viscosity and blood flow, led to the observed higher levels of tissue perfusion during extreme hemodilution.

The relative viscosity of the two RBC suspensions obtained after HV and LV protocols being different, even though the concentration of RBCs is similar, suggests the presence of interactions among the blood components. Dextrans are known to interact with RBCs as a function of molecular size (Gustafsson, et al., *Am. J. Physiol.* 241: H513–H518, 1981), and the dissimilarity between the relative viscosities of the two RBC suspensions may be indicative of either differences in the extent of RBC aggregation/adhesion and/or RBC deformability in the two suspensions. RBC aggregation could cause RBC sedimentation in horizontal venules, leading to venular occlusion, which was not observed. Moreover, because FCD was not affected by the HV protocol, it is likely that RBC aggregation is not the predominant mechanism, as this would lead to capillary occlusion by RBC aggregates and result in a decrease in FCD. Changes in RBC deformability could affect RBC distribution at vessel bifurcations; however, in the present study, capillaries without RBC flux are usually characterized by the presence of stationary RBCs. Therefore, RBC deformability does not appear to be a major factor affecting our FCD measurements. The average shear rate of 160 $s^{-1}$ used in these viscosity measurements is one at which whole blood is somewhat non-Newtonian. To test blood in a Newtonian regime, it would be more desirable to use a shear rate>500 $s^{-1}$; however, this would require a larger blood sample than is available from these small animals. The average shear rate selected is a compromise between the need to characterize blood viscosity at a shear rate that is high enough so that complex rheology is not a principal factor and the small blood samples that can be obtained from these animals. Wall shear stress was estimated following Eq. 1 and was found to be significantly higher after the HV than with the LV protocol. The significantly higher wall shear stress in arterioles stemmed from the increased blood plasma viscosity after the HV protocol since there were not differences in wall shear rate. The already increased venular wall shear rate after the HV protocol compounded with the increased blood viscosity to substantially increase wall shear stress in the venules relative to that in the LV protocol. Changes in FCD reflect mechanisms that modulate the entrance of RBCs into the capillaries and occur both in normal and diseased states. Perfusion pressure has been shown to directly affect FCD (Lindbom and Arfors, *Int. J. Microcirc. Clin. Exp.* 4: 121–127, 1985). Arteriolar vasoconstriction is a mechanism that could lead to capillary shutdown (Lindbom and Arfors, *Int. J. Microcirc. Clin. Exp.*

4:,121–127, 1985). The combined effects of arteriolar vasodilation and the relatively high level of perfusion pressure observed after the HV protocol are mechanisms leading to sustained capillary perfusion during extreme hemodilution.

Our systemic and microvascular observations after level 1 exchange are supported by previous studies of moderate or limited hemodilution. Animals in this study compensated for the progressive reduction in oxygen-carrying capacity with hyperventilation. Increasing arterial $Po_2$ and pH along with the concomitant decrease in arterial Pco2 as a function of progressive hemodilution agrees with previous findings in hamsters (Kuo and Pittman, *Am. J. Physiol.* 254: H331–H339, 1988) and other species (Messmer, et al., *Adv. Microcirc.* 4: 1–77, 1972). In our study, both HR and MAP were unchanged, a finding that concurs with previous investigations in this animal model (Mirhashemi, et al., *Am. J. Physiol.* 254: H411–H416, 1988). The decline in MAP after level 3 LV and HV may in part be due to the critically low oxygen carrying capacity of the blood at this exchange level. In the same model and tissue, Mirhashemi et al. (Mirhashemi, et al., *Am. J. Physiol.* 254: H411–H416, 1988) found that a 50% exchange with Dextran 70 did not affect arteriolar diameter, which is similar to our finding after level 1 exchange. In various anesthetized animal models and different tissue beds, large feeding arterioles similar to those in our investigation resulted in arteriolar vasoconstriction after moderate hemodilution (Hudak, et al., *Am. J. Physiol.* 257: 912–917, 1989; Kuo and Pittman, *Am. J. Physiol.* 254: H331–H339, 1988; Lipowsky and Firrell, *Am. J. Physiol.* 250: H908–H922, 1986; Tigno and Henrich, *Acta. Med. Phil.* 22: 53–58, 1986). This discrepancy may be partially due to their use of anesthetics, which has been shown to affect vascular tone in our tissue (Colantuoni, et al., *Int. J. Microcirc. Clin. Exp.* 3: 13–28, 1984) and other regulatory mechanisms in different tissues. In our study, the increase in arteriolar and venular blood velocity observed after level 1 and 2 exchange is primarily a consequence of reduced blood viscosity due to blood replacement with a less viscous fluid. This is similar to the previously reported observations by investigators from this laboratory (Mirhashemi, et al., *Am. J. Physiol.* 254: H411–H416, 1988) and in various tissues by others (Hudak, et al., *Am. J. Physiol.* 257: 912–917, 1989; Kuo and Pittman, *Am. J. Physiol.* 254: H331–H339, 1988; Lipowsky and Firrell, *Am. J. Physiol.* 250: H908–H922, 1986; Tigno and Henrich, *Acta. Med. Phil.* 22: 53–58, 1986). Our findings show that arteriolar blood flow was still increased from baseline after level 2 exchange as these vessels remained vasodilated and exhibited increased RBC velocity above baseline levels. This increase in volumetric flow was not apparent in all venular flow measurements, and on the average blood flow was only slightly increased from baseline. This discrepancy is most likely a consequence of redistribution of blood in this subcutaneous vascular network system, which characteristically has more venules than arterioles.

A significant finding in the present study is that local tissue oxygenation levels are maintained even after reduction of the systemic Hct by 60% corresponding to an absolute Hct of 19.5%. The shift of the intravascular $Po_2$ frequency distributions to higher and lower $Po_2$ in arterioles and venules, respectively, is indicative of an increased oxygen extraction. The slight rise in arteriolar $Po_2$ is a result of the elevated systemic arterial $Po_2$ brought on by hyperventilation and the increase in blood flow, decreasing circulatory transit time resulting in the delivery of blood with higher oxygen content. Oxygen tension measurements made by others using surface multiwire platinum electrodes in the same tissue and model also did not detect any difference in oxygen levels from baseline after isovolemic hemodilution with Dextran 60 to a Hct of 30% (Funk and Baldinger, *Anesthesiology* 82: 975–982, 1995; Nolte, et al., *J. Lab. Clin. Med* 130: 328–338, 1997). However, the multiwire electrode technique provides only a lumped indicator of surface oxygen levels and does not enable one to resolve between the actual oxygen distribution in the vasculature and the interstitium. Oxygen tension histograms in the multiwire electrode study showed a more homogenous tissue $Po_2$ level after hemodilution with low-molecular-weight dextran to a systemic Hct of 30% (Funk and Baldinger, *Anesthesiology* 82: 975–982, 1995; Nolte, et al., *J. Lab. Clin. Med.* 130: 328–338, 1997). Our results after level 1 exchange show a right shift and narrowing of the extravascular and arteriolar $Po_2$ histograms, which when combined with the left shift in the venous $Po_2$ distribution would not result in the more homogeneous microvascular $Po_2$ distribution observed by others (Funk and Baldinger, *Anesthesiology* 82: 975–982, 1995). Multiwire electrode measurements can only be performed after lifting the cover glass of the skinfold window and thereby exposing the tissue to atmospheric oxygen. Moreover, superfusion of the exposed tissue with saline could be another source of oxygen for the tissue and could mask the oxygen delivered by blood perfusion. Repositioning of the surface electrode would also exacerbate the oxygen diffusional fields between the tissue, superfusate, and electrode surface. These factors would lead to higher $PO_2$ measurements; paradoxically, only 4% of the measurements reported after moderate exchange with Dextran 70 were >30 mmHg after hemodilution (Nolte, et al., *J. Lab. Clin. Med.* 130: 328–338, 1997). Our findings do concur on the concept that moderate hemodilution does not cause regions of hypoxia ($Po_2$ levels <5 mmHg).

Our analysis of oxygen tension did not include the two animals that had no tissue perfusion after the level 3 LV protocol, since the phosphorescence probe needed for $Po_2$ measurements could not reach the tissue understudy. It is likely that the intravascular and perivascular $Po_2$ levels in a nonperfused tissue are close to 0 mmHg. Correction of the $Po_2$ histograms for level 3 LV to include these two animals that had no blood flow in the skinfold chamber would result in a slight left shift toward lower oxygen tensions. However, this minor readjustment would not alter our finding that local $Po_2$ levels fall after 75% hemodilution regardless of the viscosity of the dilutant and the state of tissue perfusion and is a consequence of a reduction in oxygen carrying capacity beyond the limit of compensatory mechanisms. Because of the large volume of blood exchanged in each hemodilution step, we are not able to determine if tissue oxygenation above baseline levels can be achieved in this tissue during moderate hemodilution as has been suggested by theoretical studies (Hint, *Acta Anaes. Belg.* 19: 119–138, 1968; Mirhashemi, et al., *Int. J. Microcirc. Clin. Exp.* 6: 123–136, 1987). However, others have suggested that the oxygen sensitivity of the vasculature may evoke autoregulatory mechanisms (Jackson and Duling, *Circ. Res.* 53: 515–525, 1983), thereby restricting oxygen levels to within a narrow range and thus making higher-than-baseline tissue oxygen levels unattainable.

FCD is an indicator of tissue perfusion and the homogeneity of tissue oxygenation (Lindbom and Arfors, *Int. J. Microcirc. Clin. Exp.* 4: 121–127, 1985). In the current study, we found that a higher FCD could be achieved with the HV than with the LV protocol. Our method for evaluating FCD tends to underestimate the number of capillaries perfused during extreme hemodilution, since, as the hemodilution progresses, the number of RBCs transiting decreases and may lead to a low-Hct vessel being labeled as a nonfunctional capillary. However, because the same method is used in both groups and the systemic Hct levels are the same, the finding that the HV fluid can better maintain the FCD during extreme hemodilution than the LV fluid should not be affected by this limitation in the methodology.

In a study on severe hemorrhagic shock by Kerger et al. (Kerger, et al., *Am. J. Physiol.* 270: H827–H836, 1996), maintenance of FCD was the sole critical microvascular parameter that separated surviving from nonsurviving animals. Systemic Hct was reduced to 22.5% due to autotransfusion. Thus our results suggest that reperfusion with HV plasma expanders may be beneficial in volume restitution, since the higher plasma viscosity may aid in restoring or maintaining FCD.

The present study demonstrates that replacing blood with a HV fluid at extreme hemodilution (systemic Hct of 12%) and thus returning blood viscosity toward normal results in levels of tissue perfusion that would not be achieved with lower-viscosity fluid. It is proposed that increasing plasma viscosity led to an increase in wall shear stress and along with the maintained blood flow triggered vasodilation in the microvascular bed. Direct $Po_2$ measurements using palladium-porphyrin phosphorescence quenching microscopy document for the first time that local tissue oxygenation in subcutaneous tissue is maintained after a 60% isovolemic hemodilution.

Example 4
Preparation of PEG-dextran
Dextran-poly(ethylene Glycol) Conjugates

Dextran conjugates with a variety of low-molecular-weight and high-molecular-weight are well known. Routine methods for the chemical activation of an inert dextran molecule in order to couple it further with other substances include oxidative activation with iodic acid or periodates, treatment with cyanogen bromide or cyanuric chloride. Oxidative activation leads to the formation of free aldehyde groups in dextran molecules which can be easily converted into amino-groups by a variety of methods. Amino-groups are commonly recognized as the most convenient to deal with in the process of conjugation of different chemical or biological entities and functions.

However, oxidation of a dextran molecule can easily cause its disintegration into small fragments (the phenomenon is especially pronounced when non-linear, branched dextran is used), whereas other methods involve the use of highly toxic substances which makes them unacceptable from the pharmaceutical point of view. To escape dextran disintegration in the process of periodate oxidation, this oxidation is normally permitted to proceed to a very limited degree which results in a small number of aldehyde group formed (the modification degree is usually expressed as a number of aldehyde groups per 100 dextran units) and, subsequently, in a limited number of amino-groups incorporated into dextran molecule.

A typical example of preparation of aminodextran by partial dextran oxidation and subsequent interaction of adlehydedextran with a polyamine is presented by Shin et al. (U.S. Pat. No. 5,057,313; 1991). In this patent, aminodextran was used as carrier of pharmaceutical functions. The average number of aldehyde groups recommended by the authors is 50–150 for a dextran of MW of about 40,000. As MW of a glucose unit of dextran is ca. 200, it corresponds to generation of 1 reactive group (aldehyde and then amino) per 2–4 dextran units. Really, to minimize dextran disintegration, single aldehyde group is introduced per 10–15 dextran units. We have developed a fast and simple protocol of dextran activation with free amino groups which permits to introduce free amino-group into each dextran glucose unit without any risk of dextran molecule disintegration. This protocol involves dextran modification with carbonyldiimidasole and subsequent treatment with a polyamino (preferably, ethylenediamine).

In a typical protocol, 1 g of dextran is dissolved in 30 ml of formamide, and the solution is supplemented with 5 g of carbonyldiimidasole with stirring. After 30 min incubation, 300 ml of acetone is added and the precipitate formed is washed with more acetone of a glass filter and then vacuum-dried. Dry product is redissolved in 25 ml of dimethylsulfoxide and supplemented with 10 ml of ethylenediamine with stirring. After 1 hour incubation the mixture is extensively dialyzed against water for 48 h with multiple water changes. The aminodextran formed is freeze-dried. This protocol easily leads to incorporation of 100 amino groups per 100 glucose units.

In order to obtain long-circulating conjugate which can be used as a plasma expander, the aminodextran should be further coupled with multiple molecules of single terminus-activated poly(ethylene glycol) or PEG. Commercially available methoxy-PEG (MPEG) can be used for this purpose.

In a typical protocol, 2 g of aminodextran are dissolved in 40 ml of formamine and supplemented with 0.2 ml of thriethylamine. The solution obtained under intense stirring is supplemented dropwise with the solution of 5 g of MPEG-NHS ester (N-hydroxysuccinimide ester) in 20 ml of formamide. When the reaction mixture starts to form gel, the addition of MPEG-NHS should be terminated. Small quantity (0.5 ml) of acetic anhydride is added to the reaction mixture to block the remaining free amino-groups. TNBS method is used for confirm complete disappearance of amino-groups. Conjugate is dialyzed against water for 72 hours with several changes and then freeze-dried. Product is very stable when stored at room temperature.

In the protocol described, any dextran, e.g., with MW from 5,000 to 500,000 (or even highter), can be coupled with multiple PEG chains, e.g., with MW from 1,000 to 40,000. To prepare the product with the properties preferred for using it as a plasma expander, preferable MW of dextran should be from 20,000 to 150,000, and MW of PEG should be from 2,000 to 20,000. The molecular size, viscosity, and circulation time of dextran-PEG conjugate can be easily controlled by varying the degree of dextran amination, dextran and PEG molecular weight, and the number of PEG chains grafted to a single dextran molecule.

Example 5
Use of PEG-dextran as Viscosity-increasing Agent

PEG-dextran was tested in in vivo experiments in the hamster window preparation, or hamster skinfold model, which allows observation and measurement of events that occur in the mirocirculation in terms of blood flow velocity and tissue oxygenation. This technique involves the formation of a skin fold in the back of the hamster, and the implantation of a glass window, supported by a titanium frame, which allows the observation of microvessels by video-microscopy. The animals tolerate the procedure well and observations can be made several days after the skin fold surgical intervention, and in the absence of anesthesia. The model and experimental protocol comply with all National Institutes of Health regulations for animal welfare and experimentation.

PEG-dextran was tested in the hamster model in a standard hemodilution protocol for plasma expanders, consisting of the simultaneous withdrawal of blood and infusion of the test solution. The exchange was carried to a hematocrit (Htc: concentration of red blood cells) decrease to 20% of the original value. For this species, this implies a reduction from 50% to about 10% Htc. PEG-dextran was used in the concentration of 8% weight per volume.

The animals tolerated the exchange well; blood pressure and heart rate remained normal throughout the procedures. There was no sign of thrombogenesis. Most healthy animals can sustain exchanges with colloid solutions to the levels achieved in these experiments. However, in previous experiments with dextran, when hematocrit was decreased to 20% of its original value, blood pressure decreased by 35% from normal levels.

In terms of microvascular parameters, blood flow velocity increased in the microcirculation as the exchange progressed. There was no sign of vasoconstriction; both arterioles and venules had constant diameters throughout the experiments. This was also similar to what is observed in exchanges with colloids, with the exception that functional capillary density begins to decrease in exchanges with dextran 70,000 molecular weight (a conventional plasma expander) at the 50% level of exchange and reaches a low of 35% of its original value at the 80% exchange level. Arteriolar and venular blood flows increase by 15% and remained unchanged respectively relative to normal levels. These results become particularly salient when compared to previous experiments with dextran where arteriolar and venular blood flows are reduced by 25% and 50% respectively from normal levels.

Relative blood viscosity was measured by passing blood at a constant rate through a 27 gauge needle and measuring the pressure generated. Measurements showed that at 50% Htc, viscosity of the PEG-dextraniblood mixture was 33% lower than that for whole blood.

A major finding is that the new plasma expander performs as well as the conventional materials, even though its viscosity is significantly higher. The effects found, of the order of a 25% increase in blood flow, although not extraordinarily large, is significant because increased viscosity relative to conventional plasma expanders would have been expected to cause a decrease in blood flow in these conditions by conventional thinking.

The maintenance and improvement of perfusion, and improved functional capillary density found at the 50% hemodilution level indicates that this material develops the full physiological shear stress needed for the release of shear stress generated vasodilators by the vascular wall (endothelium), thus maintaining the microcirculation open. This effect cannot be obtained with plasma expanders such as dextran, HES-starch, and Ringer's lactate as conventionally used because at the higher levels of hemodilution the heart does not increase cardiac output in proportion to the drop of viscosity, thus lowering blood pressure and signaling the microcirculation to vasoconstrict, with the consequent fall of functional capillary density and impairment of tissue oxygenation.

The fact that blood viscosity is not fully maintained at the level of that of the original blood is a matter of optimization, since PEG-dextran, due to its large hydrated volume, excludes fluid from the remaining proteins, elevating their colloid osmotic pressure, causing autotransfusion, and the subsequent dilution of blood with tissue fluid. The precise formulation in terms of concentration and amount of PEG material can be readily determined by routine testing to provide the desired or optimal viscosity effect and effect on the microcirculation.

The availability of a high viscosity plasma expander, used to maintain or increase blood viscosity, constitutes a new form of volume restitution that engages natural vasodilatory mechanisms present in the circulation, that otherwise are depressed in conditions such as hemorrhage. This material significantly improves perfusion in pathological conditions where there is perfusion deficiency.

All patents and publications mentioned in the specification are indicative of the levels of skill of those skilled in the art to which the invention pertains. All references cited in this disclosure are incorporated by reference to the same extent as if each reference had been incorporated by reference in its entirety individually.

One skilled in the art would readily appreciate that the present invention is well adapted to carry out the objects and obtain the ends and advantages mentioned, as well as those inherent therein. The specific methods and compositions described herein as presently representative of preferred embodiments are exemplary and are not intended as limitations on the scope of the invention. Changes therein and other uses will occur to those skilled in the art which are encompassed within the spirit of the invention are defined by the scope of the claims.

It will be readily apparent to one skilled in the art that varying substitutions and modifications may be made to the invention disclosed herein without departing from the scope and spirit of the invention. For example, those skilled in the art will recognize that the invention may suitably be practiced using a variety of different expression vectors and sequencing methods within the general descriptions provided.

The invention illustratively described herein suitably may be practiced in the absence of any element or elements, limitation or limitations which is not specifically disclosed herein. Thus, for example, in each instance herein any of the terms "comprising," "consisting essentially of" and "consisting of" may be replaced with either of the other two terms. The terms and expressions which have been employed are used as terms of description and not of limitation, and there is not intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

In addition, where features or aspects of the invention are described in terms of Markush groups or other grouping of alternatives, those skilled in the art will recognize that the invention is also thereby described in terms of any individual member or subgroup of members of the Markush group or other group. For example, if there are alternatives A, B, and C, all of the following possibilities are included: A separately, B separately, C separately, A and B, A and C, B and C, and A and B and C.

Thus, additional embodiments are within the scope of the invention and whiting the following claims.

What we claim is:

1. A method for increasing plasma viscosity in a mammal, comprising administering to said mammal a pharmaceutically acceptable non-oxygen-carrying viscosity increasing agent in an amount sufficient to increase peripheral viscosity by at least 2.0 centipoise.

2. The method of claim 1, wherein said mammal is a human.

3. A method for increasing plasma viscosity in a mammal, comprising administering to said mammal a pharmaceutically acceptable non-oxygen-carrying viscosity increasing agent in an amount sufficient to increase peripheral viscosity by at least 1.0 centipoise, wherein administration of said viscosity-increasing agent delays or eliminates the need for a blood transfusion.

4. A method for increasing plasma viscosity in a mammal, comprising administering to said mammal a pharmaceutically acceptable non-oxygen-carrying viscosity increasing agent in an amount sufficient to increase peripheral viscosity by at least 1.0 centipoise, wherein, either prior to or following administration of said viscosity-increasing agent, the hematocrit of said mammal is reduced by at least 50% from normal for the mammalian species.

5. A method for increasing plasma viscosity in a mammal, comprising administering to said mammal a pharmaceutically acceptable non-oxygen-carrying viscosity increasing agent in an amount sufficient to increase peripheral viscosity by at least 1.0 centipoise, wherein, either prior to or following administration of said viscosity-increasing agent, the hematocrit of said mammal is reduced by at least 50% from normal for the individual mammal.

6. A method for maintaining capillary blood flow in a mammal, comprising increasing plasma viscosity by administering to said mammal a pharmaceutically acceptable non-oxygen-carrying viscosity-increasing agent in an amount sufficient to increase plasma viscosity by at least 1.0 centipoise.

7. The method of claim 6, wherein said mammal is a human.

8. The method of claim 6, wherein said increase in plasma viscosity results in an increase in peripheral blood flow of at least 25%.

9. The method of claim 6, wherein, either prior to or following the administration of said viscosity-increasing agent, the hematocrit of said mammal is decreased by at least 50%.

10. A method for shifting the transfusion threshold in a patient, comprising administering to a patient suffering from a reduction in red blood cell concentration a pharmaceutically acceptable viscosity increasing agent in an amount sufficient to increase or maintain functional capillary density at least 60% of normal or to increase plasma viscosity at least 25% or both.

11. A method for treating a patient suffering or at risk of a condition characterized by a reduction in peripheral blood flow, comprising administering to said patient a pharmaceutically acceptable viscosity increasing agent.

12. A method for enhancing or maintaining the release of vasodilators and shear stress dependent vasodilators in the system of microscopic blood vessels of a mammal, comprising administering to said mammal a pharmaceutically acceptable non-oxygen-carrying viscosity increasing agent.

13. A method for enhancing the biological function of a hemoglobin-based artificial blood product or palsma expander that provides insufficient viscosity to maintain sufficient wall shear stress, comprising administering to a patient a non-oxygen-carrying viscosity increasing agent in conjuction with said hemoglobin-based artificial blood product or plasma expander in an amount sufficient to elevate plasma viscosity sufficiently to maintain functional capillary density in a mammalian patient at least 40% of normal.

14. The method of claim 1, wherein said viscosity increasing agent has a viscosity of at least 4.0 centipoise.

15. The method of claim 14, wherein said viscosity increasing agent has a viscosity of between 4 and 20 centipoise.

16. A method for increasing plasma viscosity in a mammal, comprising administering to said mammal a pharmaceutically acceptable non-oxygen-carrying viscosity increasing agent in an amount sufficient to increase peripheral viscosity by at least 1.0 centipoise, wherein said viscosity increasing agent has a viscosity of between 4 and 20 centipoise, and wherein said viscosity increasing agent comprises a PEG-dextran conjugate.

17. A method for increasing plasma viscosity in a mammal, comprising administering to said mammal a pharmaceutically acceptable non-oxygen-carrying viscosity increasing agent in an amount sufficient to increase peripheral viscosity by at least 1.0 centipoise, wherein said viscosity increasing agent has a viscosity of between 4 and 20 centipoise, and wherein the PEG of said PEG-dextran conjugate has an average molecular weight of between 1,000 and 40,000 daltons.

18. The method of claim 6, wherein said viscosity-increasing agent has a viscosity of at least 4.0 centipoise.

19. The method of claim 18, wherein said viscosity-increasing agent has a viscosity of between 4 and 20 centipoise.

20. The method of claim 19, wherein said viscosity-increasing agent comprises a PEG-dextran conjugate.

21. The method of claim 20, wherein the PEG of said PEG-dextran conjugate has an average molecular weight of between 1,000 and 40,000 daltons.

22. The method of claim 10, wherein said viscosity increasing agent has a viscosity of at least 4.0 centipoise.

23. The method of claim 22, wherein said viscosity increasing agent has a viscosity of between 4 and 20 centipoise.

24. The method of claim 23, wherein said viscosity increasing agent comprises a PEG-dextran conjugate.

25. The method of claim 24, wherein the PEG of said PEG-dextran conjugate has an average molecular weight of between 1,000 and 40,000 daltons.

26. The method of claim 11, wherein said viscosity increasing agent has a viscosity of at least 4.0 centipoise.

27. The method of claim 26, wherein said viscosity increasing agent has a viscosity of between 4 and 20 centipoise.

28. The method of claim 27, wherein said viscosity increasing agent comprises a PEG-dextran conjugate.

29. The method of claim 28, wherein the PEG of said PEG-dextran conjugate has an average molecular weight of between 1,000 and 40,000 daltons.

30. The method of claim 12, wherein said viscosity increasing agent has a viscosity of at least 4.0 centipoise.

31. The method of claim 30, wherein said viscosity increasing agent has a viscosity of between 4 and 20 centipoise.

32. The method of claim 31, wherein said viscosity increasing agent comprises a PEG-dextran conjugate.

33. The method of claim 32, wherein the PEG of said PEG-dextran conjugate has an average molecular weight of between 1,000 and 40,000 daltons.

34. The method of claim 13, wherein said viscosity increasing agent has a viscosity of at least 4.0 centipoise.

35. The method of claim 34, wherein said viscosity increasing agent has a viscosity of between 4 and 20 centipoise.

36. The method of claim 35, wherein said viscosity increasing agent comprises a PEG-dextran conjugate.

37. The method of claim 36, wherein the PEG of said PEG-dextran conjugate has an average molecular weight of between 1,000 and 40,000 daltons.

38. The method of claim 1, wherein said administering comprises administering said agent in an amount sufficient to increase peripheral viscosity by at least 2.5 centipoise.

39. The method of claim 1, wherein said administering comprises administering said agent in an amount sufficient to increase peripheral viscosity by at least 3 centipoise.

40. The method of claim 1, wherein said administering comprises administering said agent in an amount sufficient to increase peripheral viscosity by from 3 to 5 centipoise.

41. The method of claim 1, wherein said administering comprises administering said agent in an amount sufficient to increase peripheral viscosity by from 3.5 to 4.5 centipoise.

* * * * *